(12) United States Patent
Minosawa et al.

(10) Patent No.: US 7,841,980 B2
(45) Date of Patent: Nov. 30, 2010

(54) TREATMENT SYSTEM, TROCAR, TREATMENT METHOD AND CALIBRATION METHOD

(75) Inventors: Ryo Minosawa, Tsukui-gun (JP); Takumi Dejima, Tokyo (JP); Manabu Miyamoto, Tokyo (JP); Kiyotaka Matsuno, Sagamihara (JP)

(73) Assignee: Olympus Medical Systems Corp. (JP)

( * ) Notice: Subject to any disclaimer, the term of this patent is extended or adjusted under 35 U.S.C. 154(b) by 592 days.

(21) Appl. No.: 11/432,267

(22) Filed: May 11, 2006

(65) Prior Publication Data

US 2007/0265502 A1   Nov. 15, 2007

(51) Int. Cl.
*A61B 1/04* (2006.01)
(52) U.S. Cl. .................. 600/118; 600/103; 600/104; 600/109; 600/117; 600/424
(58) Field of Classification Search ................. 600/101, 600/103, 104, 109, 113, 114, 117, 118, 129, 600/160, 167, 173, 420, 424; 348/65; 604/117, 604/122, 158
See application file for complete search history.

(56) References Cited

U.S. PATENT DOCUMENTS

| | | | | |
|---|---|---|---|---|
| 5,417,210 A | * | 5/1995 | Funda et al. | 600/425 |
| 5,572,999 A | * | 11/1996 | Funda et al. | 600/118 |
| 5,630,431 A | * | 5/1997 | Taylor | 128/897 |
| 5,749,362 A | * | 5/1998 | Funda et al. | 600/407 |
| 5,836,869 A | * | 11/1998 | Kudo et al. | 600/173 |
| 6,036,637 A | * | 3/2000 | Kudo | 600/173 |
| 6,241,657 B1 | * | 6/2001 | Chen et al. | 600/117 |
| 6,468,265 B1 | * | 10/2002 | Evans et al. | 606/1 |
| 6,612,980 B2 | * | 9/2003 | Chen et al. | 600/117 |
| 6,648,816 B2 | | 11/2003 | Irion et al. | |
| 6,858,003 B2 | * | 2/2005 | Evans et al. | 600/103 |
| 7,537,561 B2 | * | 5/2009 | Yamaya et al. | 600/106 |

(Continued)

FOREIGN PATENT DOCUMENTS

JP   09-149879   6/1997

(Continued)

OTHER PUBLICATIONS

Letter from German associate dated Sep. 4, 2007 forwarding the Search Report dated Aug. 16, 2007 to Japanese associate, including discussion of relevancy thereof.

(Continued)

*Primary Examiner*—John P Leubecker
*Assistant Examiner*—Samuel Candler
(74) *Attorney, Agent, or Firm*—Ostrolenk Faber LLP

(57) ABSTRACT

A treatment system includes a guide component that is used to insert a treatment tool into a body cavity, a tilt sensor that is provided in the guide component and detects an angle of inclination of the treatment tool that has been inserted inside the guide component, an insertion amount sensor that is provided in the guide component and detects an amount that the treatment tool has been inserted inside the guide component, a switching device that switches an observation range of images of an interior of the body cavity that are acquired by an observation device that has been introduced into the body cavity and are then displayed on a display unit, and a system control unit that drives the switching device based on information about the angle of inclination and insertion amount of the treatment tool.

15 Claims, 19 Drawing Sheets

U.S. PATENT DOCUMENTS

2003/0009185 A1* 1/2003 Jessen .................. 606/167
2003/0135091 A1* 7/2003 Nakazawa et al. .......... 600/113
2005/0033117 A1* 2/2005 Ozaki et al. ............. 600/109

FOREIGN PATENT DOCUMENTS

| JP | 09149879 A | * | 6/1997 |
| JP | 2005021353 A | * | 1/2005 |
| JP | 2005021354 A | * | 1/2005 |
| JP | 2005021355 A | * | 1/2005 |

OTHER PUBLICATIONS

Search Report issued by European Patent Office on Aug. 16, 2007 in connection with corresponding European patent application No. EP 07 00 9436.

* cited by examiner

TREATMENT SYSTEM, TROCAR, TREATMENT METHOD AND CALIBRATION METHOD

BACKGROUND OF THE INVENTION

1. Field of the Invention

The present invention relates to a system used to treat an organism, a treatment method, a trocar that is used in this treatment, and a calibration method.

2. Description of Related Art

When performing a medical practice (including observation and treatment—the same applies below) on a human internal organ or the like, a treatment method is known in which, instead of making a large incision in the abdominal wall, a plurality of apertures are opened in the abdominal wall and a surgical procedure is then performed by inserting treatment tools such as an endoscope and forceps individually into each of the apertures. In this treatment method, because only small apertures need to be opened, this method has the advantages that there is little invasiveness and the recovery of the patient is rapid.

While treatment is being performed, the field of view of the operator is secured by images obtained from the endoscope. However, because the hands of the operator are occupied with operating the treatment tools, tasks such as moving the field of view of the endoscope and adjusting the focus and zoom thereof, are performed by an assistant known as a scopist. Because of this, the assistant must operate the endoscope without obstructing the work of the operator and also ensure the field of view of the operator inside the body cavity.

Here, a structure has also been developed in which, instead of an assistant operating the endoscope, the endoscope is able to move automatically. The control unit for the endoscope controls movements of the endoscope such that the endoscope constantly tracks marks that are provided at the distal end of a treatment tool. The position of the marks is calculated using image processing after setting the color of the marks as an object color for extraction. The endoscope then causes the position of the CCD to move such that the marks on the treatment tool are always in the center of a rectangular range that forms the image range.

SUMMARY OF THE INVENTION

It is an object of the present invention to provide a structure in which, when an image of a treatment tool that has been inserted into a body is obtained using an endoscope so as to secure the range of view of an operator, the image obtained by the endoscope is appropriately switched in accordance with the movement of the treatment tool so that the treatment tool can be reliably tracked.

The treatment system according to the first aspect of the present invention includes: a guide component that is used to insert a treatment tool into a body cavity; a tilt sensor that is provided in the guide component and detects an angle of inclination of the treatment tool that has been inserted inside the guide component; an insertion amount sensor that is provided in the guide component and detects an amount that the treatment tool has been inserted inside the guide component; a switching device that switches an observation range of images of an interior of the body cavity that are acquired by an observation device that has been introduced into the body cavity and are then displayed on a display unit; and a system control unit that drives the switching device based on information about the angle of inclination and insertion amount of the treatment tool.

The treatment method according to the second aspect of the present invention includes the steps of: detecting an insertion amount when a treatment tool is inserted through a guide component that has been made to pierce an abdominal wall; detecting an angle of inclination of the guide component; inserting an observation device into a body cavity through a second guide component that has been made to pierce the abdominal wall; and switching an observation range of image of the body cavity interior which is displayed on a display unit and which is acquired by the observation device that has been introduced into the body cavity based on an angle of inclination and an insertion amount of the treatment tool.

The trocar according to the third aspect of the present invention includes: a mantle tube through which a treatment tool can be inserted is inserted into a body cavity through an abdominal wall; a head portion that has a hole through which the treatment tool can be inserted and that is provided with a valve that isolates the body cavity interior from the body exterior; an insertion sensor that is provided in the mantle tube and detects an insertion amount of the treatment tool; and a tilt sensor that, using the gravitational direction as a reference, detects an angle of inclination of the mantle tube that is inclined together with the treatment tool.

The calibration method according to the fourth aspect of the present invention is used to correlate a position of a guide component that pierces an abdominal wall in order for a treatment tool to be introduced into a body cavity with a position of an observation device inserted into the body cavity, and includes the steps of: acquiring an insertion amount and an angle of inclination of an adjustment tool inserted into a body cavity through the guide component; acquiring an image of the distal end component of the adjustment tool using the observation device; calculating a position and size of the distal end component using image processing; and calculating a position of the guide component based on the position and size of the distal end component acquired at three or more different positions and from the insertion amount and angle of inclination of the adjustment tool at each position.

DETAILED DESCRIPTION OF THE INVENTION

Embodiments of the present invention will now be described. Note that the same symbols are applied to the same component elements in each embodiment and any duplicated description thereof is omitted.

First Embodiment

Figure 1:
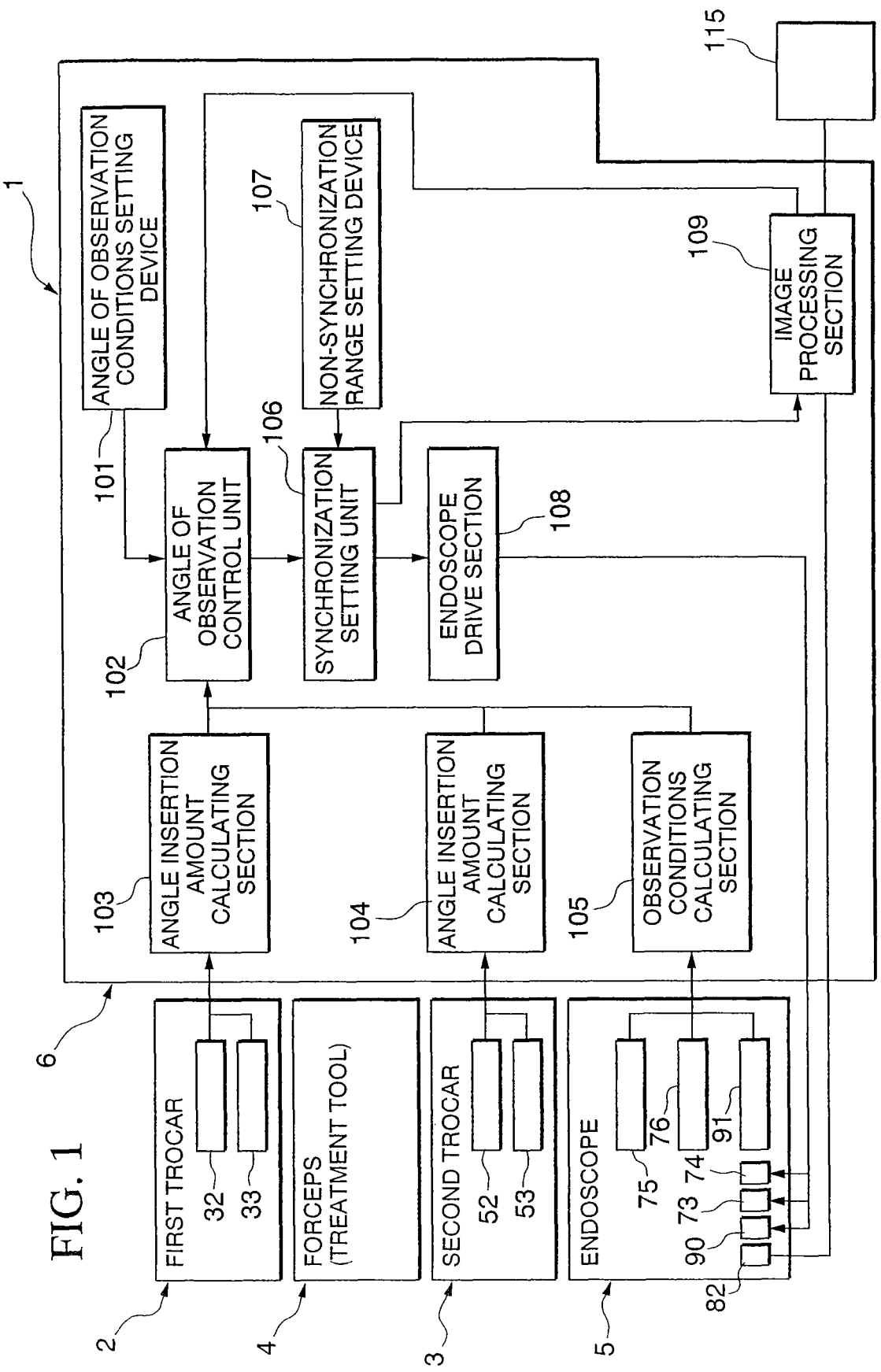
FIG. 1 is a block diagram showing the overall structure of a treatment system.

The schematic structure of a treatment system is shown in FIG. 1. The treatment system 1 has a first trocar 2 and a second trocar 3 that are inserted through an abdominal wall AW of a patient, forceps (i.e. a treatment tool) 4 that are inserted through the first trocar 2, an observation device in the form of an endoscope 5 that is inserted through the second trocar 3, and a system control unit 6 that is connected to each of the trocars 2 and 3 and the endoscope 5.

Figure 2:
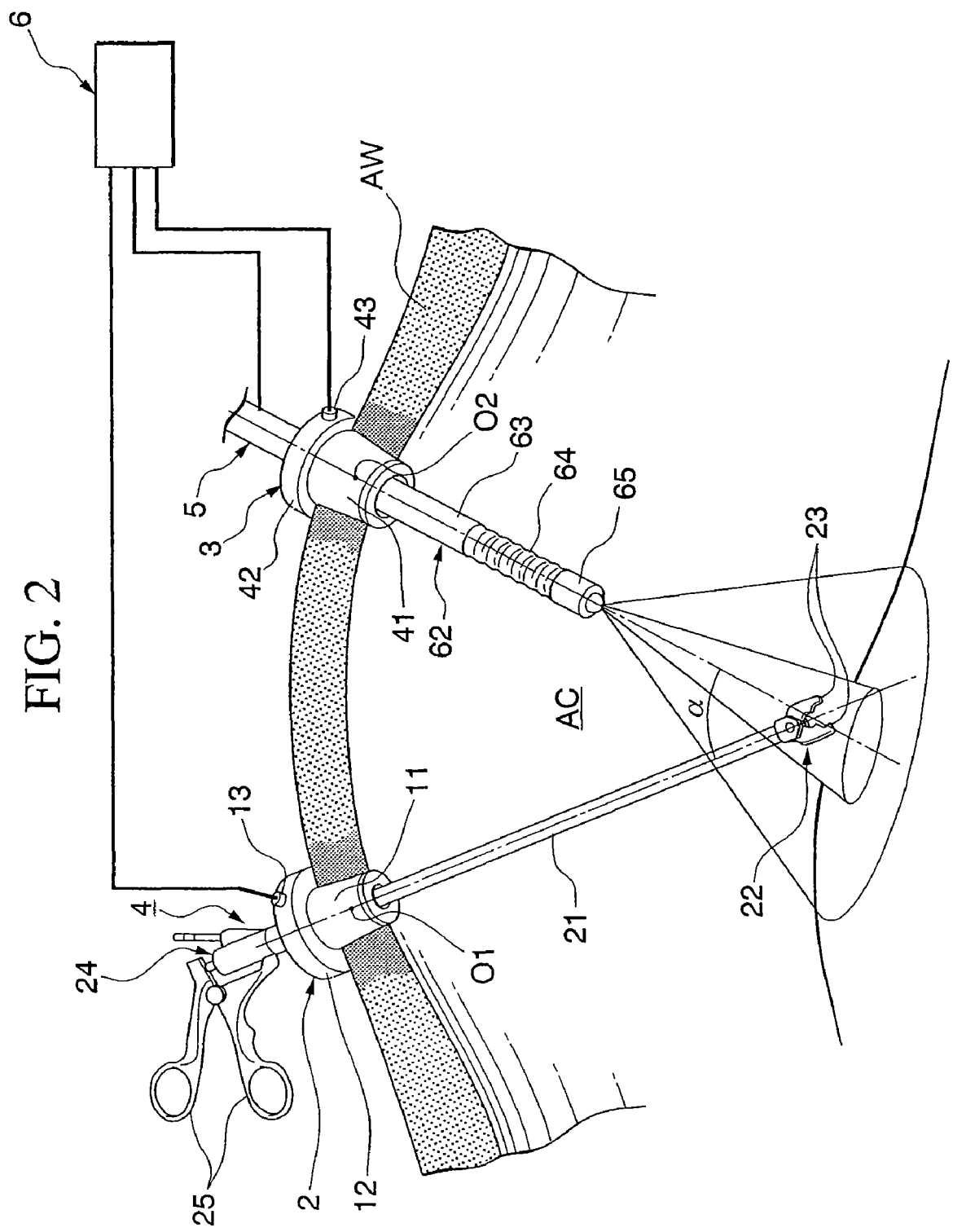
FIG. 2 is a view illustrating placement during treatment.

As is shown in FIG. 2, the first trocar 2 has a mantle tube 11 whose distal end is inserted into an abdominal cavity AC through the abdominal wall AW, and a head portion 12 that remains external to the body. The first trocar 2 is a guiding component that guides a treatment tool in the form of the forceps 4 into the abdominal cavity AC. The mantle tube 11 is formed as a circular cylinder and is removably attached to the head portion 12. The head portion 12 is manufactured so as to have a larger diameter than the mantle tube 11. An airtight valve (not shown) that forms a division between the abdominal cavity AC and the body exterior is formed inside the head portion 12. Moreover, a terminal 13 that is connected to the system control unit 6 is provided at an external circumferential surface of the head portion 12. Because the mantle tube 11 is removably attached to the head portion 12, the mantle tube 11 can be discarded and the head portion 12 that is provided with the airtight valve and the like can be reused. However, it is also possible for the mantle tube 11 and the head portion 12 to be formed as a single body.

The forceps 4 have a narrow, elongated insertion portion 21 that is inserted into the abdominal cavity AC through the first trocar 2, and a treatment portion 22 is provided at a distal end of the insertion portion 21. The treatment portion 22 has a pair of forcep components 23 that can open and close freely. The opening and closing of the forcep components 23 is driven by the forward and backward movement of an operating component (not shown) that passes inside the insertion portion 21. The forward and backward operation of the operating component is achieved using an operating portion 24 that is provided at a base end of the insertion portion 21. The operating portion 24 is provided with a pair of freely opening and closing handles 25 that are gripped by an operator. When an operator grasps the handles 25 and closes them, the pair of forcep components are also closed. When the handles 25 are opened, the pair of forcep components are also opened. Note that the treatment tool may also be a high frequency knife or a snare or the like and is not limited to the forceps 4.

Figure 3:
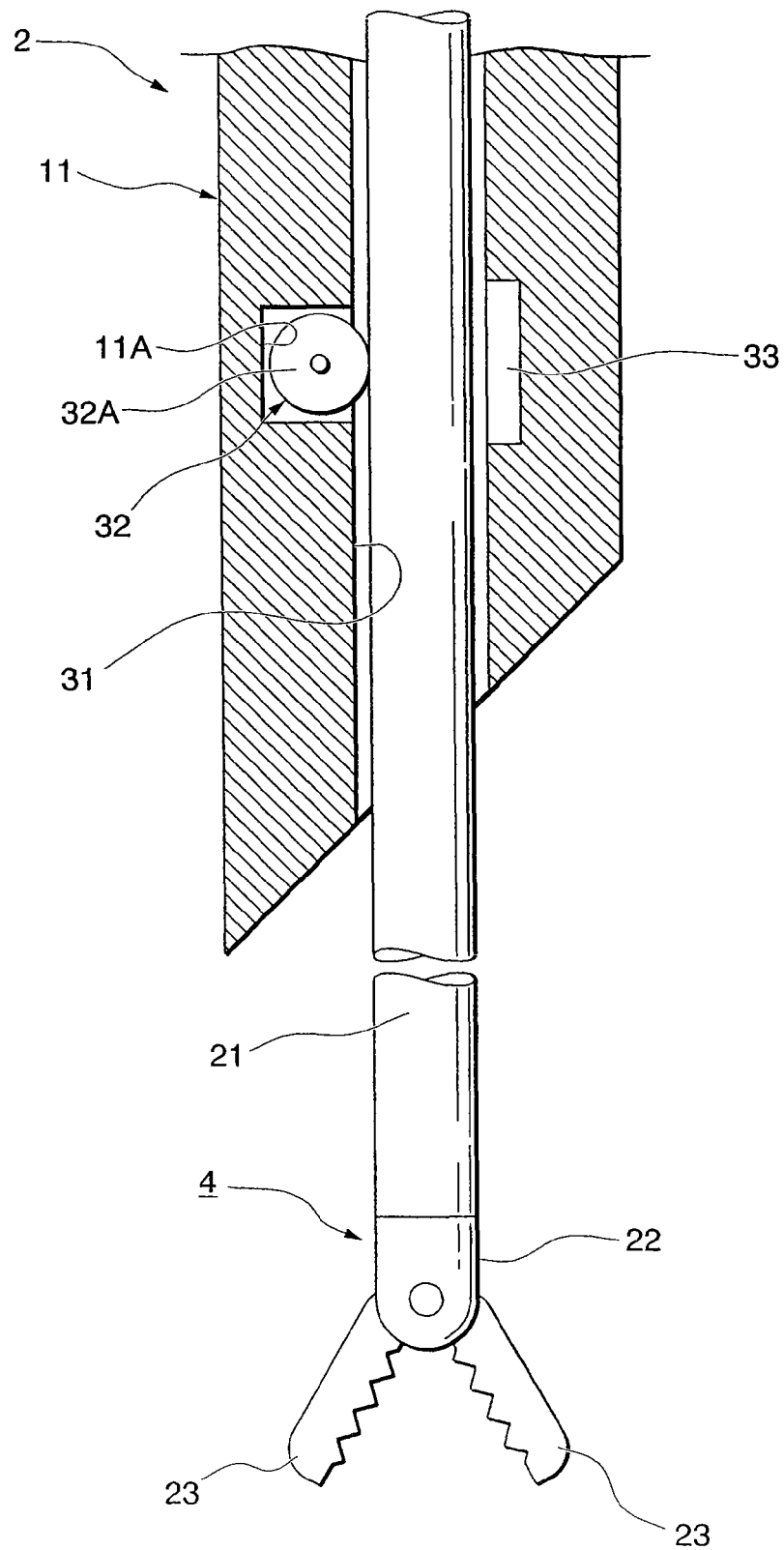
FIG. 3 is a cross-sectional view of a distal end portion of a first trocar.

Here, as is shown in FIG. 3, a hole 31 through which the forceps 4 can be moved forward or backward freely is formed penetrating the mantle tube 11 of the first trocar 2 and extending in the longitudinal direction thereof. Furthermore, an insertion quantity sensor 32 that detects an insertion amount of the forceps 4 and a tilt sensor 33 that detects an angle of inclination of the first trocar 2 are incorporated at an inner circumferential side of the hole 31. The mounting positions of the sensors 32 and 33 are preferably positions that form base points when the first trocar 2 is tilted or positions provided in the vicinity thereof, however, they may also be mounted at the distal end side or the base end side of the mantle tube 11.

A rotary encoder that has a rotor 32A is used for the insertion quantity sensor 32. The rotor 32A is placed inside a housing portion 11A that is recessed inside the mantle tube 11, and is supported such that it can rotate freely around an axis that is substantially orthogonal to the longitudinal direction of the mantle tube 11, namely, orthogonal to the insertion direction of the forceps 4. The outer circumferential surface of the rotor 32A is located so as to not be in contact with the mantle tube 11 but so as to be in contact with the outer circumferential surface of the forceps 4 that have been inserted into the hole 31. Because the rotor 32A is rotated by the insertion portion 21 when the forceps 4 are inserted, the insertion quantity sensor 32 outputs a signal that corresponds to the rotation amount of the rotor 32A.

The tilt sensor 33 is formed by a biaxial acceleration sensor that is able to detect tilt in two directions that are each orthogonal to the gravitational direction, and outputs signals that correspond to the angle of inclination relative to the gravitational direction. Outputs from the tilt sensor 33 and outputs from the insertion quantity sensor 32 are sent from the terminal 13 of the head portion 12 to the system control unit 6 via the inside of the mantle tube 11.

Figure 4:
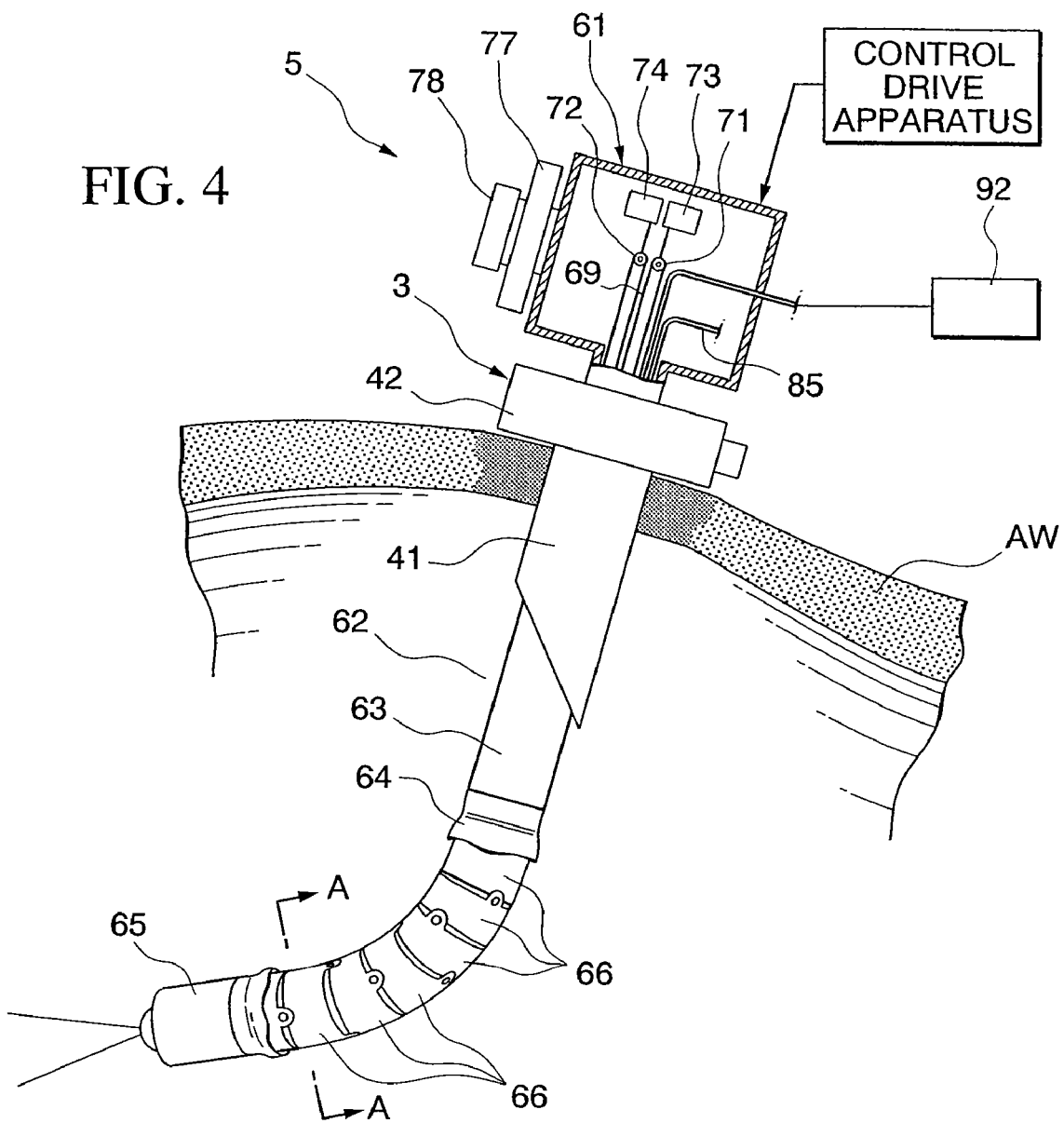
FIG. 4 is a view showing the schematic structure when a portion of the endoscope is shown as a cross section.

As is shown in FIGS. 1, 2, and 4, the second trocar 3 has a mantle tube 41 whose distal end is inserted into the abdominal cavity AC through the abdominal wall AW, and a head portion 42 that has a large enough diameter to allow the mantle tube 41 to be removably fitted therein. The second trocar 3 is a guiding component that guides the endoscope 5 into the abdominal cavity AC. The structure of the second trocar 3 is substantially the same as that of the first trocar 2, and an insertion quantity sensor 52 that detects an insertion amount of the endoscope 5 and a tilt sensor 53 that detects an angle of inclination of the second trocar 3 are incorporated in the mantle tube 41. Signals from these sensors are output from a terminal 43 on the head portion 42. A rotary encode is used for the insertion quantity sensor 52. A biaxial acceleration sensor is used for the tilt sensor 53. In the second trocar 3, the mantle tube 41 can be discarded, while the head portion 42 can be reused. The mantle tube 41 and the head portion 42 may also be formed as a single body.

In the endoscope 5, an insertion portion 62 that is inserted into a body interior extends from an operating portion 61 that is used outside the body. The insertion portion 62 has a hard portion 63 that is inserted into the second trocar 3, and a bending portion 64 (i.e., a switching device) that is provided at a tip of the hard portion 63. An image pickup device 65 is mounted at a distal end of the bending portion 64. The bending portion 64 is constructed by linking together in the longitudinal direction substantially toroidal bending barrels 66. The positions where two bending frames 66 are joined together are each shifted 90 degrees in a circumferential direction around the axis line.

Figure 5:
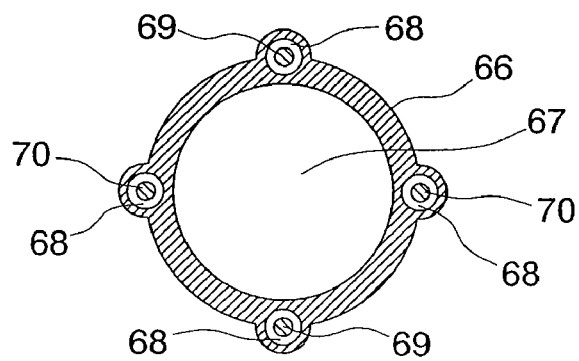
FIG. 5 is a cross-sectional view taken along the line A-A in FIG. 4.

As is shown in FIG. 5, each bending barrel 66 is formed by a toroidal component having a through hole 67 in the center thereof, and a cable such as the image pickup device 65 passes through the through hole 67. Four holes 68 are provided equidistantly in the circumferential direction of the bending barrels 66. One of two wires 69 and 70 is made to pass through each of the holes 68. The first wire 69 has one end portion fixed to the foremost bending barrel 66 and is guided to the interior of the operating section 61 through those holes 68 from among the holes 68 in the respective bending barrels 66 that are placed at the same positions in the circumferential direction. Inside the operating section 61, the first wire 69 is trained around a pulley 71 and is then once again guided inside the insertion portion 62. It is then made to pass through the holes 68 located on the opposite side from the holes 68 which it passed through previously. The other end portion of the wire 69 is fixed to the foremost bending barrel 66. The second wire 70 is trained around another pulley 72 inside the operating portion 61. Both the one end portion and the other end portion of the wire 70 are passed through holes 68 located in positions offset by 90 degrees from the first wire 69, and are fixed to the foremost bending barrel 66.

The two pulleys 71 and 72 are linked respectively to a rotation shaft of one of two motors 73 and 74 that are located inside the operating section 61. For example, if the motor 73 is rotated so that the one end portion of the first wire 69 is pulled and the other end portion is pushed, then the bending portion 64 is bent in an up-down direction (i.e., a first direction). If the other motor 74 is rotated so that the one end portion of the second wire 70 is pulled and the other end portion is pushed, then the bending portion 64 is bent in a left-right direction (i.e., a second direction that is orthogonal to the first direction). The drive amount and drive direction of the respective wires 69 and 70 can be detected by the sensors 75 and 76 shown in FIG. 1. A rotary encoder such as, for example, the one that detects the rotation amount of the motors 73 and 74 can be used for the sensors 75 and 76, however, other types of sensor may also be used. Note that because the respective pulleys 71 and 72 are formed such that they can be individually linked to either of two knobs 77 and 78 that are provided at an outer side portion of the operating section 61, it is also possible for the operator or assistant to perform the bending operation manually.

Figure 6:
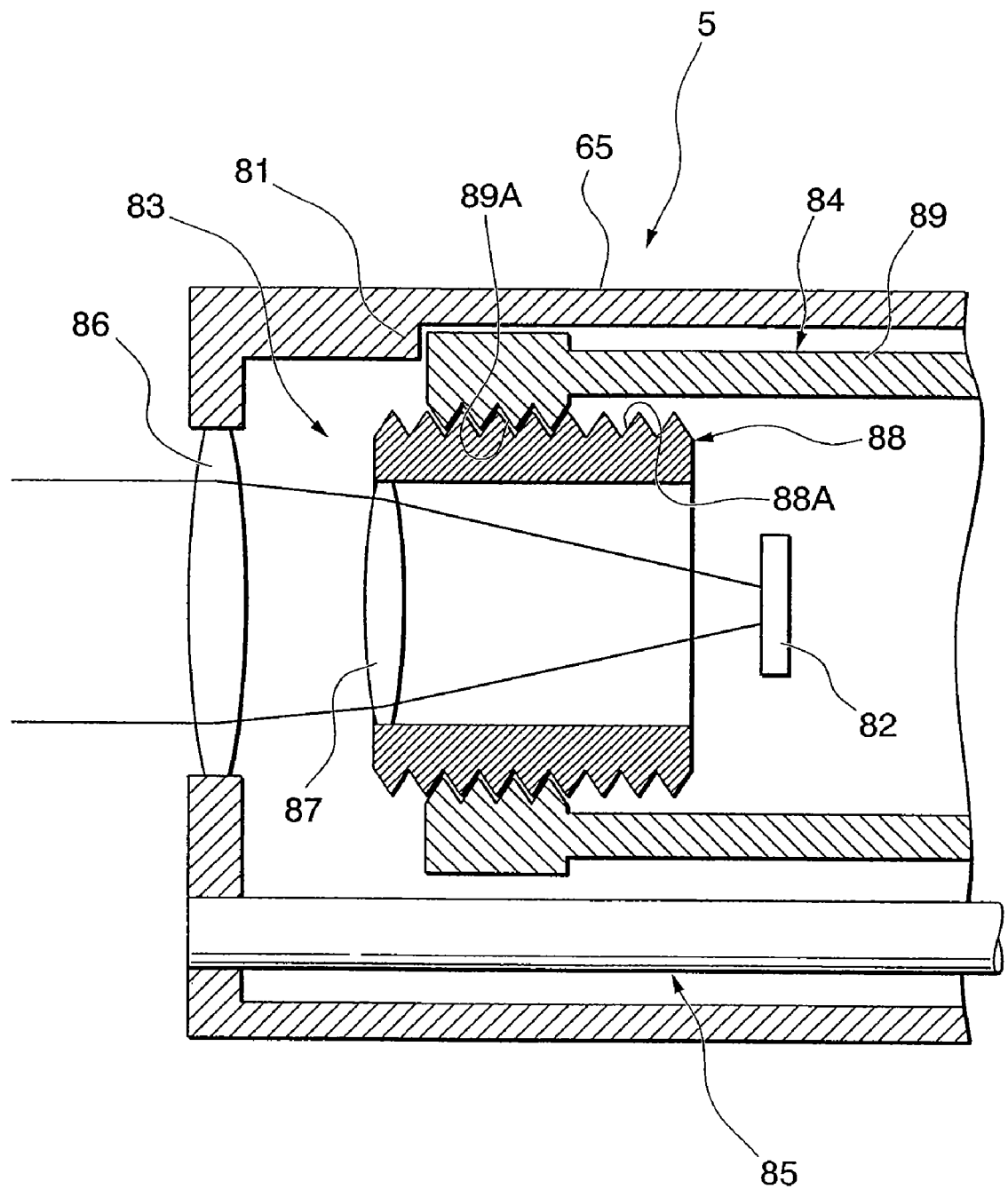
FIG. 6 is a cross-sectional view showing the structure of an image pickup device at the distal end of an endoscope.

The schematic structure of the image pickup device 65 that is provided at the distal end of the insertion portion 62 is shown in FIG. 6. The image pickup device 65 has an image pickup element in the form of a CCD 82, a magnifying optical system 83, a zoom apparatus 84 (i.e., a switching device) that moves the magnifying optical system 83, and an illumination apparatus 85 that illuminates the interior of the abdominal cavity AC that are each provided inside a cover 81. The magnifying optical system 83 has an objective lens 86 that is fixed to a distal end of the cover 81, and a movable lens 87 that is placed inside the cover 81 between the objective lens 86 and the CCD 82. A cylindrical lens stage 88 that holds the movable lens 87 has a thread 88A engraved in the outer circumference thereof, and this thread 88A meshes with a feeding thread 89A that is formed in an inner circumference of a cylinder body 89 that forms the zoom apparatus 84. The cylinder body 89 extends in the direction of the optical axis and is supported by the cover 81 so as to be able to freely rotate around the optical axis. If the cylinder body 89 is rotated by the motor 90 shown in FIG. 1 around the optical axis, the lens stage 88 is moved in the axial direction so that the moveable lens 87 can approach or move away from the CCD 82. The position of the movable lens 87, namely, the magnification of the magnifying optical system 83 can be detected by the sensor 91. A rotary encoder that, for example, detects the rotation amount and rotation direction of the motor 90 can be used for the sensor 91, however, other types of sensor may also be used. The illumination apparatus 85 has an optical fiber and is able to guide illumination light from a light source that is located outside the body. Note that the zoom apparatus 84 may also be a piezoelectric actuator that holds the movable lens 87 and makes a forward or backward movement when energized.

The system control unit shown in FIG. 1 has an angle of observation conditions setting device 101, an angle of observation control unit 102, two angle insertion amount calculating sections 103 and 104, an observation conditions calculating section 105, a synchronization control unit 106, a non-synchronization range setting device 107, and an endoscope drive section 108.

The angle of observation conditions setting device 101 is an input device that sets conditions when an image of the forceps 4 is being picked up by the image pickup device 65. Here, the conditions are set such that an angle α that is formed between the forceps 4 and the center of the visual field of the observation range of the endoscope 5 (i.e., the center of the observation image displayed on a monitor 115) is kept at a substantially constant angle. In addition to this, the angle formed between the forceps 4 and the center of the visual field of the endoscope 5 and the magnification and the like can be altered during an observation as is desired. The angle of observation conditions setting device 101 is a device for selecting and inputting numerical values, however, it may also be a knob or switch that is provided on the operating section 61 of the endoscope 5.

The angle insertion amount calculation section 103 receives outputs from the respective sensors 32 and 33 of the first trocar 2 and calculates insertion quantities and angles of inclination for the forceps 4. These calculation results are then output to the observation angle control unit 102. In the same way, the angle insertion amount calculation section 104 receives outputs from the respective sensors 52 and 53 of the second trocar 3 and calculates insertion quantities and angles of inclination for the endoscope 5. These calculation results are then also output to the observation angle control unit 102.

The observation conditions setting section 105 calculates the state of the bend in the bending portion 64 of the endoscope 5, namely, calculates the position of the image pickup device 65 using the hard portion 63 of the endoscope 5 as a reference. The position of the image pickup device 65 is checked by the sensors 75 and 76, and is calculated from the direction and amounts that the wires 69 and 70 are pulled from a state in which the bending portion 64 extends in a straight line. In addition, the zoom magnification of the image pickup device 65 is calculated from detection results from the sensor 91.

The angle of observation control unit 102 calculates image pickup conditions based on information from the two angle insertion amount calculation sections 103 and 104 and on information from the observation conditions calculating section 105 and the angle of observation conditions setting device 101, and outputs these conditions to the synchronization control unit 106.

The synchronization control unit 106 determines whether or not the visual field of the image pickup device 65 is in synchronization with or is not in synchronization with the movement of the forceps 4 based on information that is input into the non-synchronization range setting device 107.

The non-synchronization range setting device 107 is an input device that is used for inputting a range where the forceps 4 and the visual field of the image pickup device 65 are not to be in synchronization. The input information may be in a variety of formats such as numerical values showing a range, or information to select a predetermined range. It is also possible for the non-synchronization range setting device 107 and the angle of observation conditions setting device 101 to be the same input device.

The endoscope drive section 108 controls the motors 73 and 74 that are used for bending operations and controls the motor 90 of the zoom apparatus 84 of the image pickup device 65.

The system control unit 6 has an image processing section 109 (i.e., a switching device) that processes image signals from the CCD 82 of the image pickup device 65, and causes observation images to be displayed on the monitor 115.

Notes that the endoscope drive section 108 and the observation conditions calculating section 105 may also be provided inside an operating section 51 of the endoscope 5. It is also possible for the endoscope drive section 108 and the observation conditions calculating section 105 to be formed as a totally separate endoscope control unit together with the illumination apparatus of the endoscope 5.

Figure 7:
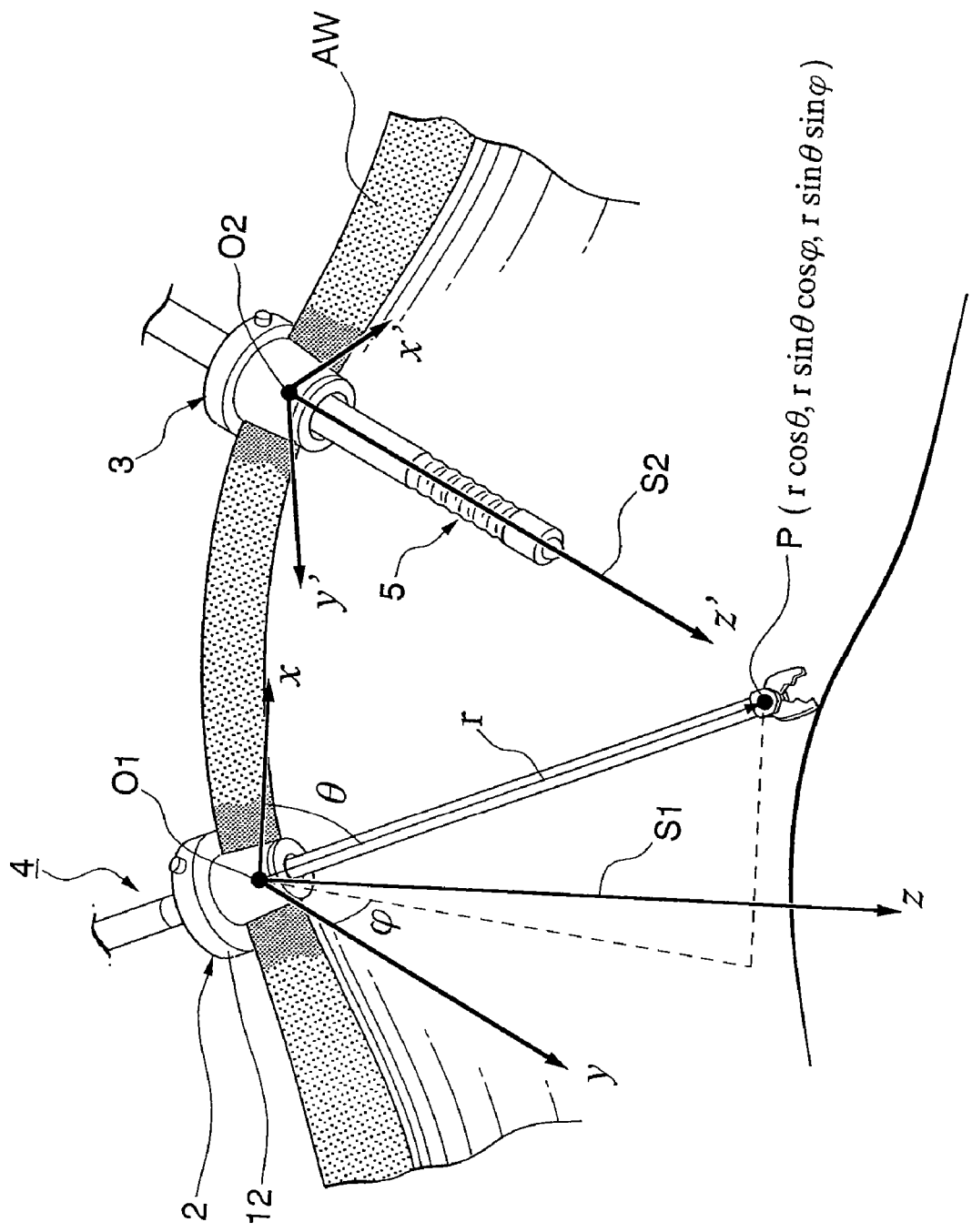
FIG. 7 is a typical view showing a coordinate system taking a first trocar as a reference and a coordinate system taking a second trocar as a reference.

Here, a description will be given with reference made to FIG. 7 and FIG. 8 of the logic used to associate the position of the distal end of the forceps 4 with the observation position of the endoscope 5. As is shown in FIG. 7, in a coordinate system S1 for the forceps 4, a base point O1 of the first trocar 2 is taken as the point of origin, while the gravitational direction is taken as the z axis, while two axes that are orthogonal to the z axis are taken as the x axis and the y axis. The coordinates (x, y, z) of the position P of the distal end of the forceps in the coordinate system S1 can be expressed as:

$$x = r \cos \phi$$

$$y = r \sin \theta \cos \phi$$

$$z = r \sin \theta \sin \phi.$$

Note that θ is an angle formed between the x axis and a vector running from the base point O1 to a point P, while φ is an angle formed between the y axis and a vector running from the base point O1 to a point P when this vector is projected onto a yz plane. Both θ and φ are known quantities that can be detected by the tilt sensor 33 of the first trocar 2. A distance r from the base point O1 to the point P is a known amount that can be measured by the insertion quantity sensor 32.

In contrast, in a coordinate system S2 for the endoscope 5, a base point O2 of the second trocar 3 is taken as the point of origin, while the optical axis direction of the image pickup device 65 namely, the center of the visual field is taken as the z' axis, while two axes that are orthogonal to the z' axis are taken as the x' axis and the y' axis.

Accordingly, if it is possible to express the coordinates (x' p, y', p, z', p) of the position P of the distal end of the forceps 4 in the coordinate system S2 for the second trocar 3 using the parameters for the coordinate system S1 for the forceps 4, then it is possible to associate the position of the distal end of the forceps 4 with the observation position of the endoscope 5.

Figure 8:
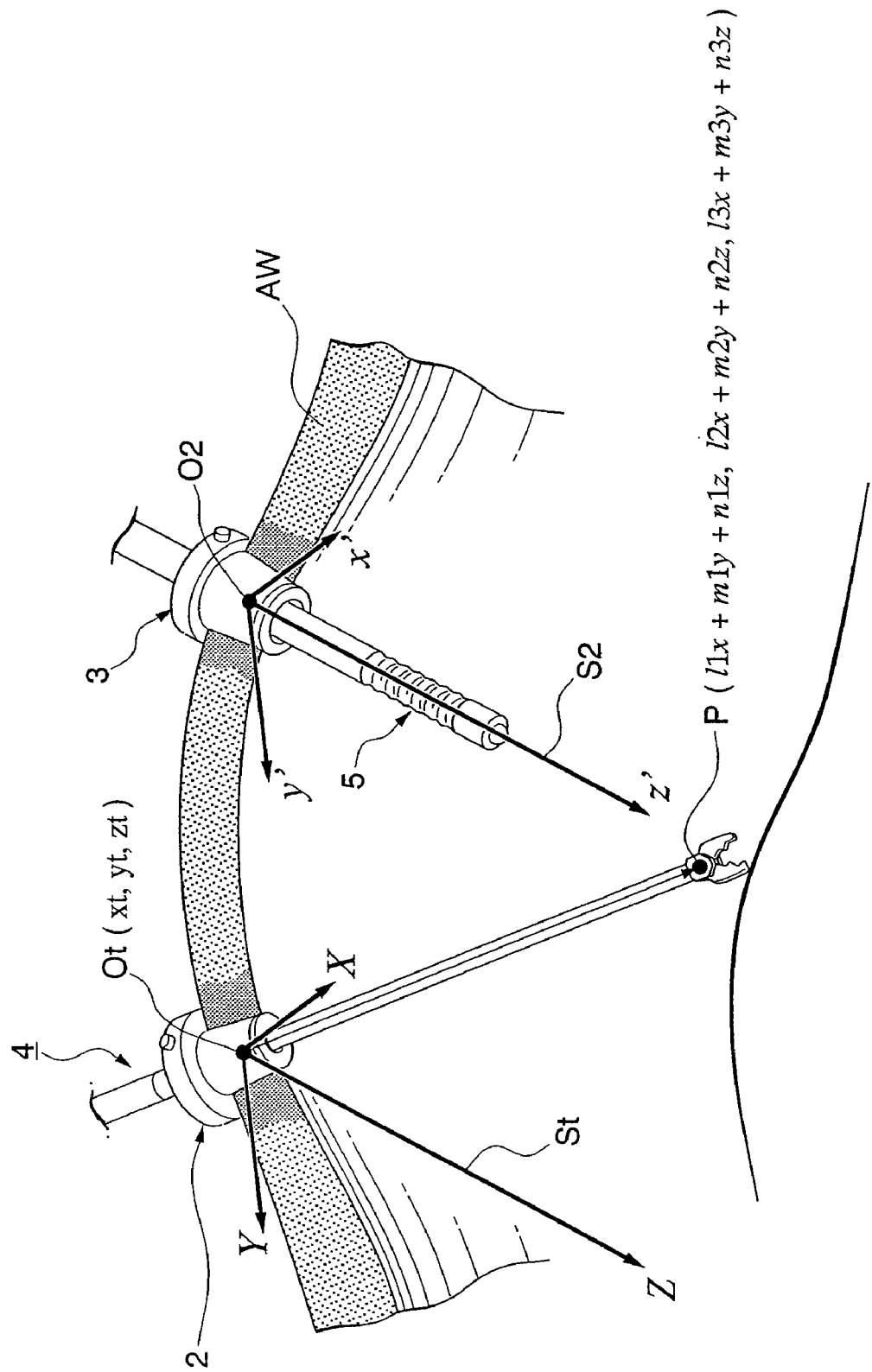
FIG. 8 is a typical view showing coordinates of the position of the distal end of a treatment tool when the coordinate system of the second trocar is moved to the first trocar.

Firstly, as is shown in FIG. 8, if the coordinate system S2 for the endoscope 5 is made to move in parallel with the coordinate system S1 for the forceps 4, then in a new coordinate system St that takes the base point O2 as its point of origin, the coordinates (Xp, Yp, Zp) of the position P of the distal end can be expressed using a direction cosine as:

$$Xp = l1 \times x + m1 \times y + n1 \times z$$

$$Yp = l2 \times x + m2 \times y + n2 \times z$$

$$Zp = l3 \times x + m3 \times y + n3 \times z.$$

Note that a relationship of l1×l1+m1×m1+n1×n1=1 is established between the direction cosine (l1, m1, n1). In the same way, a relationship of l2×l2+m2×m2+n2×n2=1 is established between the direction cosine (l2, m2, n2), and a relationship of l3×l3+m3×m3+n3×n3=1 is established between the direction cosine (l3, m3, n3).

Accordingly, if the coordinates of the position P of the distal end are expressed by the new coordinate system St using (r, θ, and φ) as parameters, then $$Xp = l1 \times r \cos \theta + m1 \times r \sin \theta \cos \phi + n1 \times r \sin \theta \cos \phi,$$

$$Yp = l2 \times r \cos \theta + m2 \times r \sin \theta \cos \phi + n2 \times r \sin \theta \cos \phi,$$

$$Zp = l3 \times r \cos \theta + m3 \times r \sin \theta \cos \phi + n3 \times r \sin \theta \cos \phi.$$

The (Xp, Yp, Zp) in the new coordinate system St are expressed as Xp=x' p−xt, Yp=y' p−yt, Zp=z' p−zt when the coordinates of a base point Ot of the first trocar 2 as seen from the point of origin O2 are taken as (xt, yt, zt). Accordingly, when the new coordinate system St is converted to the coordinate system S2 for the endoscope 5, the coordinates (x', y', z') of P are;

$$x'p = l1 \times r \cos \theta + m1 \times r \sin \theta \cos \phi + n1 \times r \sin \theta \cos \phi + xt$$

$$y'p = l2 \times r \cos \theta + m2 \times r \sin \theta \cos \phi + n2 \times r \sin \theta \cos \phi + yt$$

$$z'p = l3 \times r \cos \theta + m3 \times r \sin \theta \cos \phi + n3 \times r \sin \theta \cos \phi + zt.$$

In the initial stages, because the direction cosine and the base point (xt, yt, zt) of the forceps 4 as seen from the coordinate system S2 of the endoscope 5 are unclear, calibration is performed prior to treatment commencing so that the position of the first trocar 2 relative to the endoscope 5 is recognized in the system.

Figure 9:
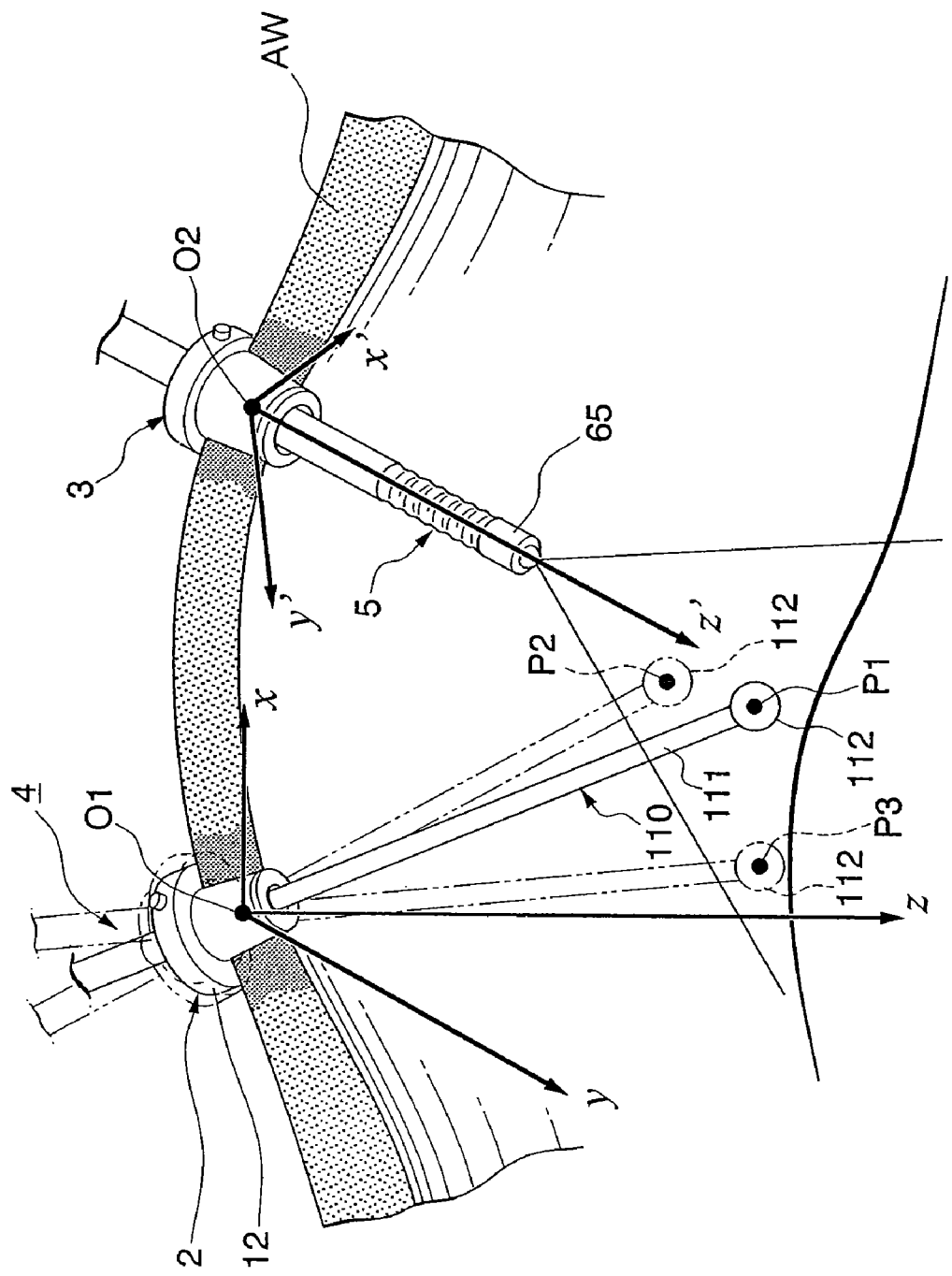
FIG. 9 is a view illustrating calibration.

When performing calibration, as is shown in FIG. 9, the endoscope 5 is inserted into the second trocar 3 that is piercing the abdominal wall AW, and an adjustment tool 110 for calibration is inserted in the first trocar 2. The adjustment tool 110 has a spherical distal end component 112 fixed to a distal end of a narrow elongated pole 111. A component whose outer diameter is already known is used for the distal end component 112.

The adjustment tool 110 is inserted into the abdominal cavity AC via the first trocar 2, and the distal end component 112 is placed at a first position P1 that is located within a range (referred to below as an image pickup capable range) that makes it possible for an image of the distal end component 112 to be picked up by the image pickup device 65 of the endoscope 5. The insertion quantity sensor 32 of the first trocar 2 detects the insertion amount of the adjustment tool 110, namely, detects the distance from the distal end component 112 to the insertion quantity sensor 32. The angle of inclination of the adjustment tool 110 relative to the gravitational direction is detected by the tilt sensor 33.

The image processing section 109 of the system control unit 6 uses image processing to calculate the central position of the distal end component 112 within the image pickup capable range and the diameter of the distal end component 112. Note that the distance from the endoscope 5 to the distal end component 112 is found from the on-screen size of the distal end component 112. This is because, on the screen, the distal end component 112 appears smaller the further away it is from the endoscope 5, and appears larger the closer it is to the endoscope 5.

Once a relation between the position of the distal end component 112 and the insertion amount and angle of inclination of the distal end component 112 has been obtained and stored in the angle of observation control unit 102, the distal end component 112 is moved to a second position P2, which is a separate position within the same image pickup capable range. In the same way, a relation between the position of the distal end component 112 and the insertion amount and angle of inclination of the distal end component 112 is also obtained for the second position P2 and is then stored. Furthermore, the distal end component 112 is then moved to a third position P3, which is a separate position within the same image pickup capable range, and a relation between the third position P3 and the insertion amount and angle of inclination of the distal end component 112 is also obtained and is then stored.

The base point O1 (=Ot) of the first trocar 2 is calculated from the respective positions and distances of the first to third positions P1 to P3. The base point O1 is determined to be a point where virtual lines that are centered respectively on one of the first to third positions P1 to P3, and that each have the respective insertion quantities as their radius intersect each other. Furthermore, the gravitational direction (i.e., a vertically downward direction) is calculated from the base point O1 and the angle of inclination at least one of the first to third positions P1 to P3. As a result, taking the position (i.e., the base point O1) of the first trocar 2 as seen from the endoscope 5 as a reference, the position of the distal end of the forceps 4 can be recognized from the angle of inclination of the first trocar 2 relative to a vertically downward direction and the insertion amount of the forceps 4.

Next, an operation is performed by inserting the forceps 4 in place of the adjustment tool 110. The processing at this time is described with reference made mainly to the flowchart shown in FIG. 10. During this processing, the second trocar 3 and the endoscope 5 are not moved manually.

Firstly, the insertion quantity sensor 32 detects the insertion amount of the forceps 4 (step S101). At the same time or at approximately the same time as this, the tilt sensor 33 detects the tilt of the first trocar 2, namely, the tilt of the forceps 3 relative to the gravitational direction (step S102). Information from the respective sensors 32 and 33 is input into the angle insertion amount calculating section 103 and the angle insertion amount calculating section 103 calculates the angle of inclination and the insertion amount of the forceps 4. Upon receiving the result of this calculation the angle of observation control unit 102 calculates the amount of movement of the distal end of the forceps 4 (step S103). In the initial state, the position of the distal end of the forceps 4 is calculated, while in subsequent processing, the amount of movement (i.e., the amount of change) of the distal end of the forceps 4 is calculated.

After this the synchronization control unit 106 determines whether or not the position of the distal end of the forceps 4 has moved within a preset range (step S104). This preset range is a range that is set by the non-synchronization range setting device 107 and within this range may be taken as being, for example, within the display screen of the monitor 115. When the position of the distal end of the forceps 4 after the movement is contained within the display screen (i.e., when the result of the determination in step S104 is YES), then because the range has been set as a non-synchronization range, the synchronization control unit 106 does not output a command signal to the endoscope drive section 108 commanding that the field of view be altered. The field of view of the endoscope 5 is thus not switched (step S105) and observation is performed in this existing state (step S107) (the processing here is omitted).

Figure 11:
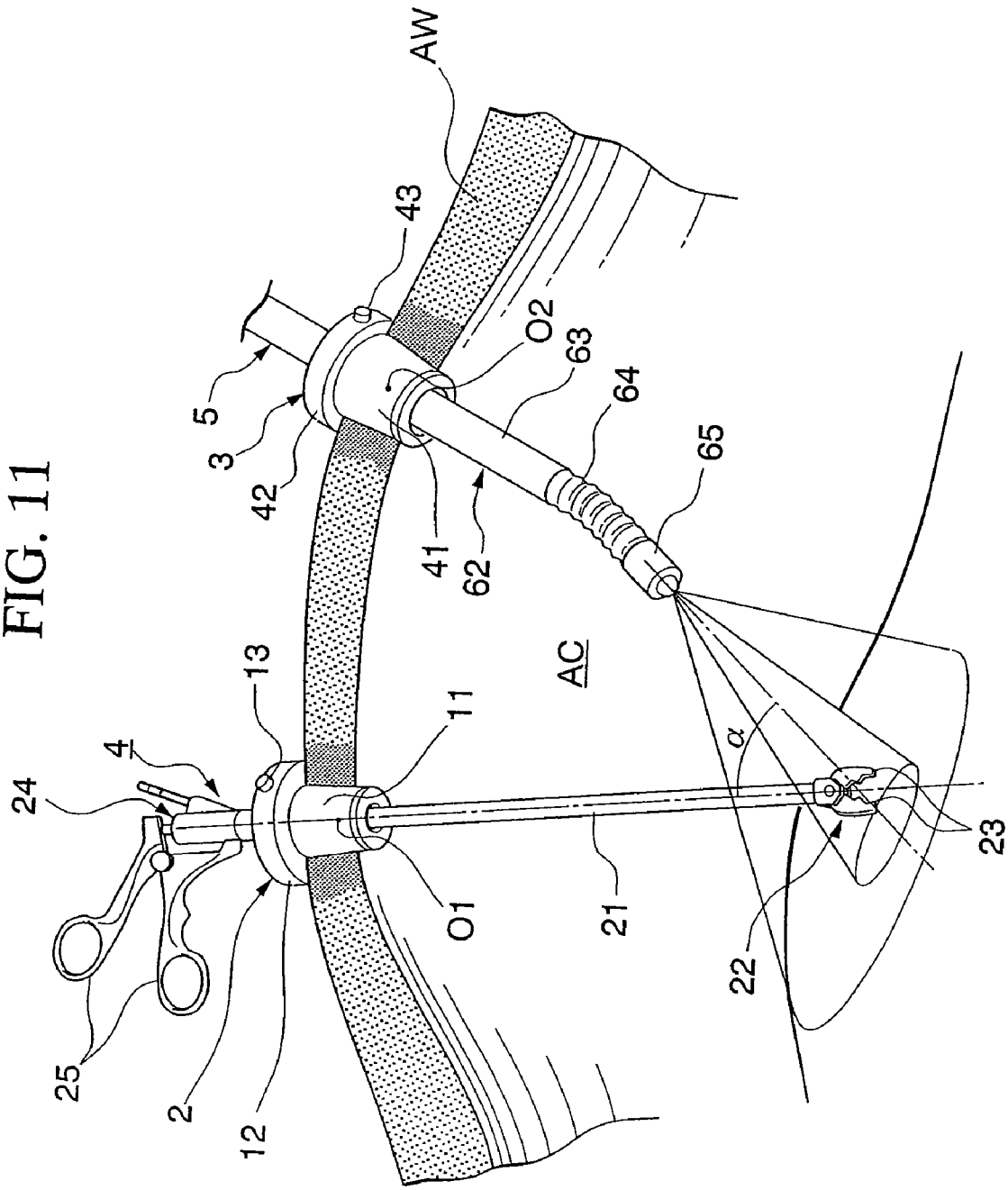
FIG. 11 is a view showing a bending portion being bent to match the movement of a treatment tool.

In contrast to this, when the position of the distal end of the forceps 4 after the movement is outside the preset range (i.e., when the result of the determination in step S104 is NO), then because the observation image needs to be synchronized with the position of the distal end of the forceps 4, the synchronization control unit 106 outputs a command signal to the endoscope drive section 108 commanding that the field of view be switched. As is shown in FIG. 11, the endoscope drive section 108 drives the endoscope 5 such that the distal end of the forceps 4 moves to the center of the observation image (step S106). Observation is then carried out in the new field of view (step S107) (the processing here is omitted). This processing is performed repeatedly.

Figure 12:
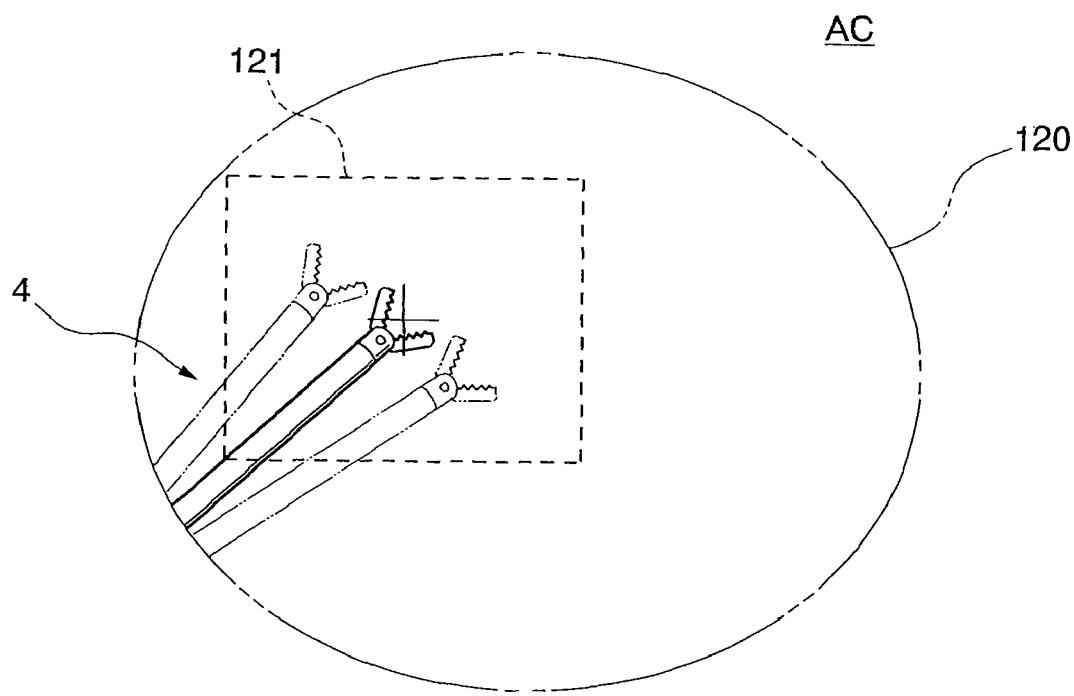
FIG. 12 is a view illustrating what happens when an observation image does not track the distal end of a treatment tool.

Here, an example of the display screen when the field of view is not switched is shown in FIG. 12. FIG. 12 shows a case in which a portion of an image pickup capable range 120 (i.e., the range of the field of view of the image pickup device 65) inside the abdominal cavity AC is displayed on the screen of the monitor 115 as an observation range 121. The observation range 121 matches the area displayed on the screen. If the position of the distal end of the forceps 4 is then moved from the center of the observation range 121 to a position that is still within the observation range 121, as is shown by the broken line, the observation range 121 is not moved. Namely, the distal end portion of the forceps 4 that is displayed in the center of the screen is displayed in a position that is offset from the center.

Figure 13:
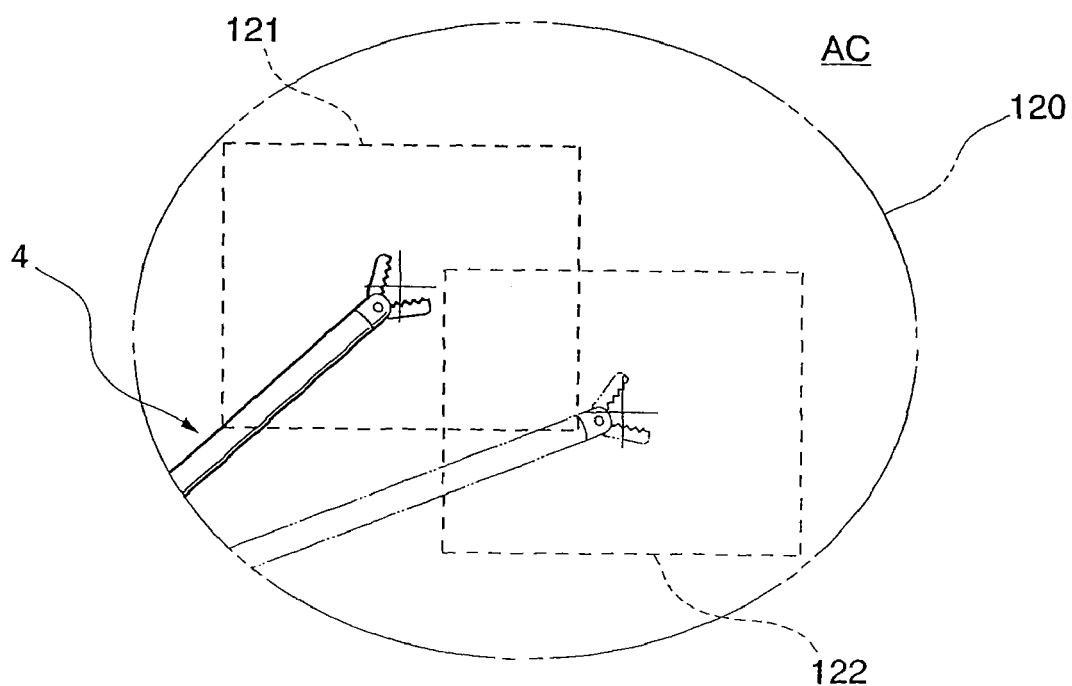
FIG. 13 is a view illustrating what happens when an observation image switches so as to track the distal end of a treatment tool.

In contrast to this, as is shown in FIG. 13, if the position of the distal end of the forceps 4 is moved to a position outside the observation range 121, the observation range switches to an observation range 122 so that the position of the distal end of the forceps 4 moves to the center of the display screen. Namely, the position of the distal end of the forceps 4 does not change from the center of the screen either before or after the forceps 4 are moved, and only the image surrounding the position of the distal end of the forceps 4 changes relatively.

The range where the synchronization or non-synchronization of the position of the distal end of the forceps 4 is switched is limited to the size of the display screen. For example, if the forceps 4 are displayed at the edge of the display screen so that operations are difficult to perform, a range that is narrower than the display screen (for example, a circle that is centered on the display screen and is contained within the display screen) is set by the non-synchronization range setting device 107. When the forceps 4 move within a range that is contained within the display screen but is at the edge of the display screen, the field of view is switched and the position of the distal end of the forceps 4 is displayed in the center of the screen.

In this treatment system 1, in order to switch the observation range such that the position within the observation range remains constant and follows the forceps 4, any of the following methods may be used. Namely, bending the endoscope 4, altering the display range (i.e., switching images) on the monitor 115, and making an enlargement or reduction using the zoom apparatus 84. These methods may selected in a variety of modes such as when settings are made so that the angle α formed between the forceps 4 and the direction of the field of view of the observation range 121 is constant, and such as when these settings are not made.

If the angle α is not set so as to be constant, then the bend in the endoscope 4 is formed such that the distal end of the forceps 4 is in the center of the observation range when the forceps 4 have been moved. Alternatively, the image may be cut out. If it is sufficient simply to change the size within the observation range, then enlargement or contraction may be performed. It is also possible to use a combination of two or more methods.

In order to simplify understanding when the angle α is set so as to be constant, firstly, a case in which the distal end of the forceps 4 is moved in a direction that is orthogonal to a straight line passing through the center of the observation range and a case in which the distal end of the forceps 4 is moved over a straight line passing through the center of the observation range will be described.

Figure 14:
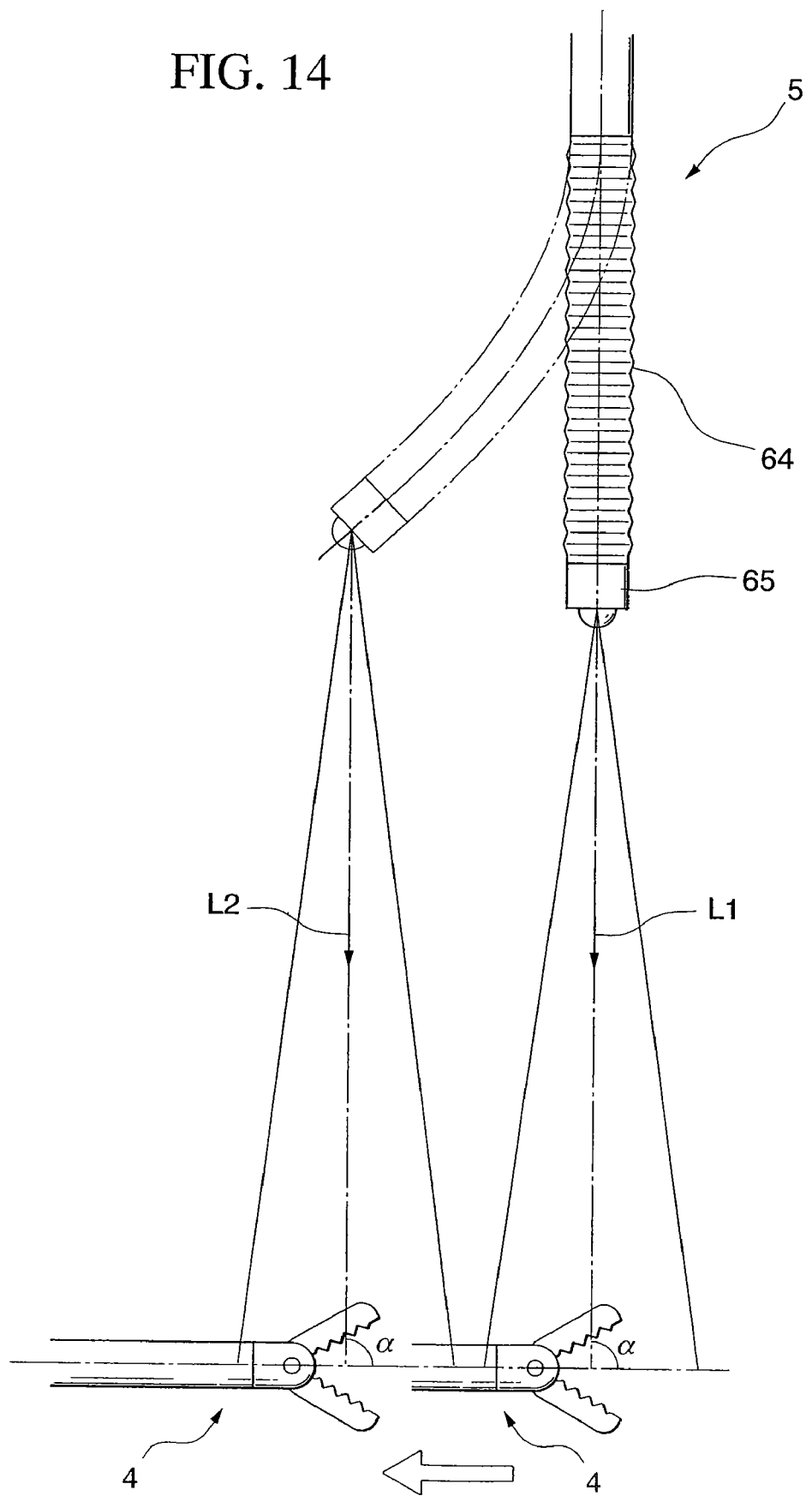
FIG. 14 is a view illustrating an operation to make an observation image track the distal end of a treatment tool when the treatment tool is making a parallel movement.

As is shown in FIG. 14, when the forceps 4 are moved in a direction that is orthogonal to the center of the observation range, the bending portion 64 of the endoscope 4 is bent. The bending portion 64 is bent such that virtual lines L1 and L2 that connect the center of the forceps 4 and the center of the endoscope 5 are parallel before and after the movement at a position that enables the angle α to be obtained in the range of the field of view. In this case, because the angle cc cannot be preserved simply by moving the bending portion 64, the angle α is preserved by the image processing section 109 cutting out a portion of the image acquired by the image pickup device 65. Note that even if the observation range prior to the movement is the portion of the image acquired by the image pickup device 65 that was cut out by the image processing section 109, then, in the same way, the angle α can be preserved by using a combination of the bending the endoscope 5 and the processing by the image processing section 109. If an operator desires to adjust the size of the forceps 4 that is displayed on the screen, the zoom apparatus 84 is used.

Figure 15:
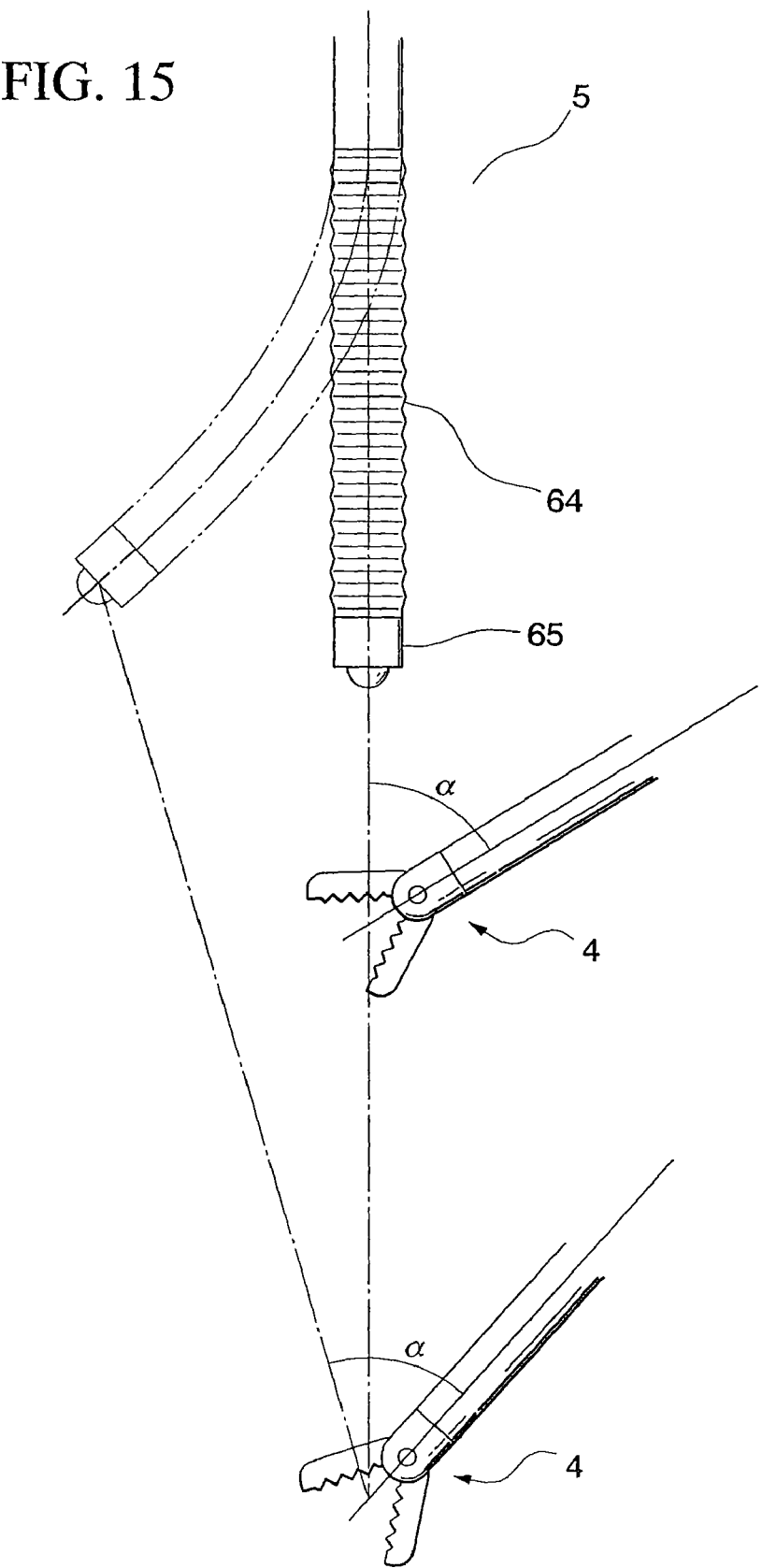
FIG. 15 is a view illustrating an operation to make an observation image track the distal end of a treatment tool when the treatment tool is moved away.

As is shown in FIG. 15, when the forceps 4 are moved such that the distal end of the forceps 4 moves away from the endoscope 5, then the angle cc is changed if only image processing or zooming is used. Therefore, the bending portion 64 is operated. The bending portion 64 moves the image pickup device 65 to a position that enables the angle α to be preserved in the range of the field of vision. Furthermore, using image processing, the image is cut out and displayed. The same processing can be performed when the distal end of the forceps 4 moves closer to the endoscope 5.

Next, a case in which the distal end of the forceps 4 is moved three-dimensionally can be achieved by combining the above two cases. In a case in which the distal end of the forceps 4 is moved three-dimensionally, because it may be possible to preserve the angle a solely by performing a bending operation, or solely by cutting out and displaying an image using image processing, or solely by performing zoom adjustment, in such cases it is sufficient if any one or two of these methods are used. In all cases, it is possible for an electronic zoom that is achieved by performing processing using the image processing section 109 to be employed for the switching device instead of the zoom apparatus 84, or in combination with the zoom apparatus 84.

Note that the selection of the switching method may be made by the optimum method being selected automatically by the angle of observation control unit 102 in accordance with the position of the distal end of the forceps 4. Alternatively, precedence may be given to a method and this method may be selected by the angle of observation conditions setting device 101.

In this manner, an operation is performed while an image of the interior of the abdominal cavity AC is acquired by the endoscope 5 in association with the forceps 4. Incisions and excisions are performed while the target portions are confirmed on the monitor 115. If necessary, the treatment tools may be substituted so that tissue can be withdrawn or so that an incision can be sutured. During this time, the endoscope 5 acquires images of the interior of the abdominal cavity AC corresponding to the respective treatment tools and operations and displays them on the monitor 115. After an operation has been completed, the endoscope and the treatment tools such as the forceps 4 and the like are withdrawn. Furthermore, after the first and second trocars 2 and 3 have been withdrawn, the apertures in the abdominal wall AW can be closed if necessary and the treatment is ended.

According to this embodiment, because the insertion quantity sensor 32 and the tilt sensor 33 are provided in the first trocar 2 and the position of the distal end of the forceps 4 is determined from the angle of inclination of the first trocar 2 and the insertion amount of the forceps 4, processing is simplified compared with when images of markings are picked up so that the distal end of the forceps 4 can be tracked using image processing, as in the conventional method. In a method in which markings are recognized, as in the conventional method, if marking images cannot be picked up due to bleeding during an operation or due to the markings being obscured by other organs, then it is not possible to make the observation images follow the forceps, however, this sort of problem is solved by this embodiment. Moreover, conventionally, if the forceps are moved faster than the speed of processing to recognize the markings, or faster than the speed at which the endoscope is actually moved, then the markings are lost from view and the endoscope cannot be made to follow the markings. However, in this embodiment, because it is possible to ascertain the position of the distal end of the forceps 4 using information from the first trocar 2 side, even if the forceps 4 temporarily move outside of the observation field of view, it is still possible for the observation range to be reliably switched so that the forceps 4 are not lost from view. Note that this embodiment also has the advantage that, because special forceps on which markings have been formed and devices for applying the markings are not required, there is a reduction in manufacturing costs and an improvement in general applicability.

Because the angle of observation conditions setting device 101 is provided so that the observation direction of the endoscope 5 and the direction of the forceps 4 can be set, it is easy for an operator to obtain useful observation images. In particular, if settings are made such that the angle α that is formed between the distal end portion of the forceps 4 and the direction of the field of view of the observation range of the endoscope 5 is kept substantially constant before and after the forceps 4 are moved, then, unlike in the conventional structure, the forceps themselves do not create a blind spot and obscure a portion that is essential for an operation so that the operation is made easier. Furthermore, it becomes easier for an operator to ascertain the progress of a treatment.

Within the range that is set by the non-synchronization range setting device 107, because the endoscope 5 is not made to track the movement of the forceps 4, it is possible to prevent the observation image from moving slightly to match any slight movement of the forceps, as in the conventional structure, which often results in the image becoming more difficult to view. In this embodiment, because the images of the internal organs and the like are fixed even if the forceps 4 are moved, it is easy to verify the state of progress and the like of an operation. Note that, if the forceps 4 are moved to the edge of an observation image so as to become difficult to see while still remaining within the range set as the non-synchronization range, then by altering the range set as the non-synchronization range, it is possible to easily acquire an image of the required field of view.

Because contact type rotary encoders are used for the insertion quantity sensors 32 and 52 of the first and second trocars 2 and 3, a simple structure can be used to detect the insertion quantities of the forceps 4 and endoscope 5. Because biaxial acceleration sensors are used for the tilt sensors 33 and 53, the angle of inclination of the forceps 4 and the angle of inclination of the endoscope 5 can be detected cheaply as amounts of inclination from the gravitational direction.

Figure 16:
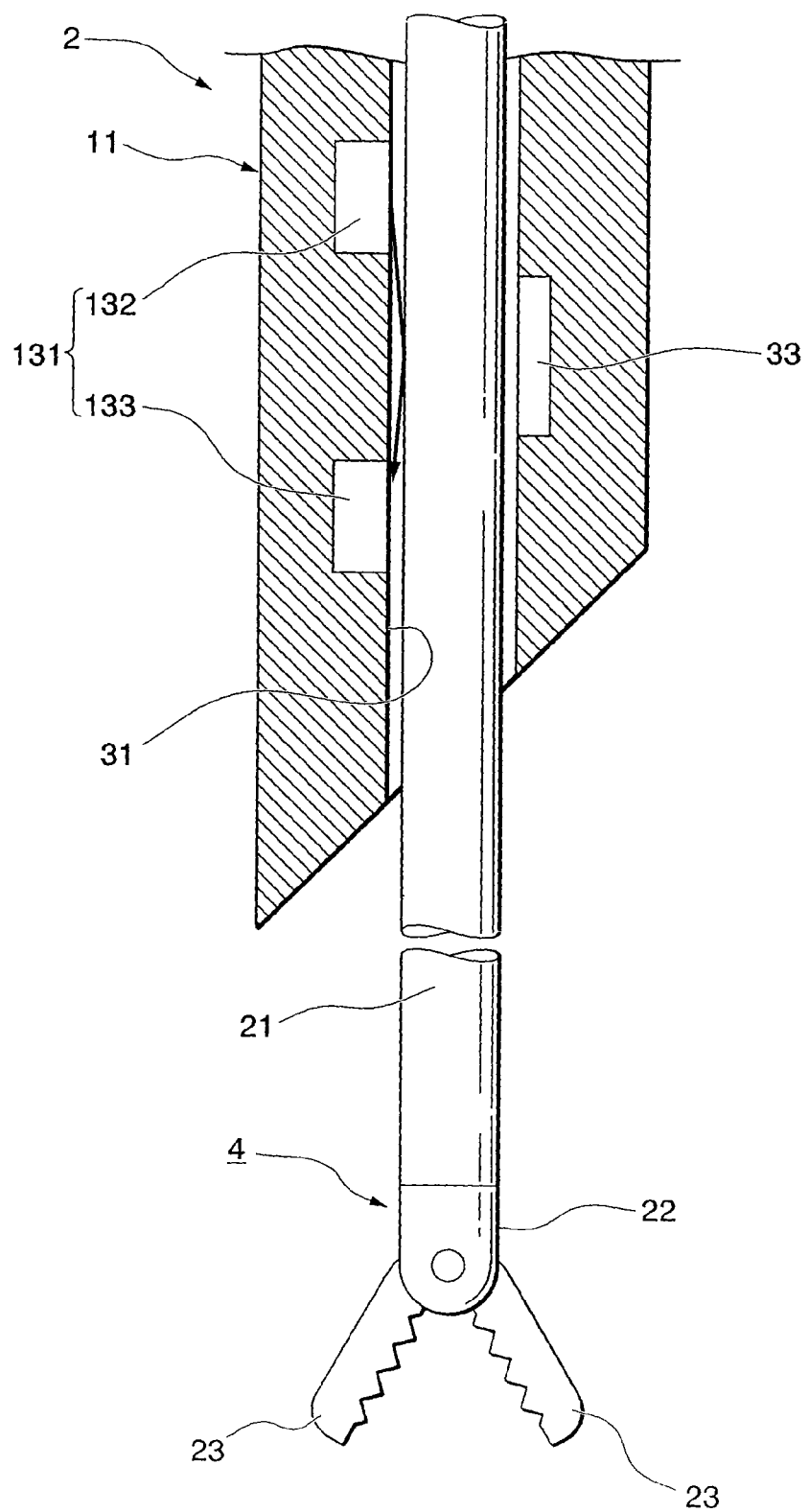
FIG. 16 is a cross-sectional view of a distal end portion of the first trocar.

Here, the insertion quantity sensors 52 and 53 may also be optical sensors. The insertion quantity sensor 131 shown in FIG. 16 may be formed by combining a light emitting element 132 with a light receiving element 133 that receives reflected light that was generated by the light emitting element 132 and was then reflected by the insertion portion 21 of the forceps 4. If, for example, a semiconductor laser is used for the light emitting element 132 then a photodiode is used for the light receiving element 133. In this insertion quantity sensor 131, changes in the intensity of the reflected light that is reflected by the forceps 4 are detected, and the insertion quantity of the forceps 4 may be measured by calculating the amount of movement of portions where the reflectance is low. The same effects as those described above are obtained even if this optical type of insertion quantity sensor 131 is used. Furthermore, because the insertion quantity can be detected without making contact, there is no wear and the insertion quantity can be accurately detected irrespective of the shape of the forceps 4.

Because the any one or more of the bending portion 64, the image processing section 109, and the zoom apparatus 84 may be used for the observation range switching device, the observation range can be switched to track the position of the distal end of the forceps 4. In particular, by using the zoom apparatus 84 of the image pickup device 65 or an electronic zoom of the image processing section 109, the distal end of the forceps 4 can be displayed on the monitor 115 always at the same size. As a result, it is easier for an operator to provide treatment. Note that if, in the image pickup device 65, the image pickup range is altered using, for example, a field of vision angle altering device that switches the field of vision angle between a wide angle and a narrow angle by moving a lens using an actuator or using a CCD (i.e., an image pickup device) in which a function of altering the image pickup range by changing the orientation of the light receiving surface by moving the CCD is provided, then even if the forceps 4 are moved to an even wider range, the forceps 4 can be displayed under fixed conditions. It is also possible for an electronic zoom function to be used in combination with this.

Figure 17:
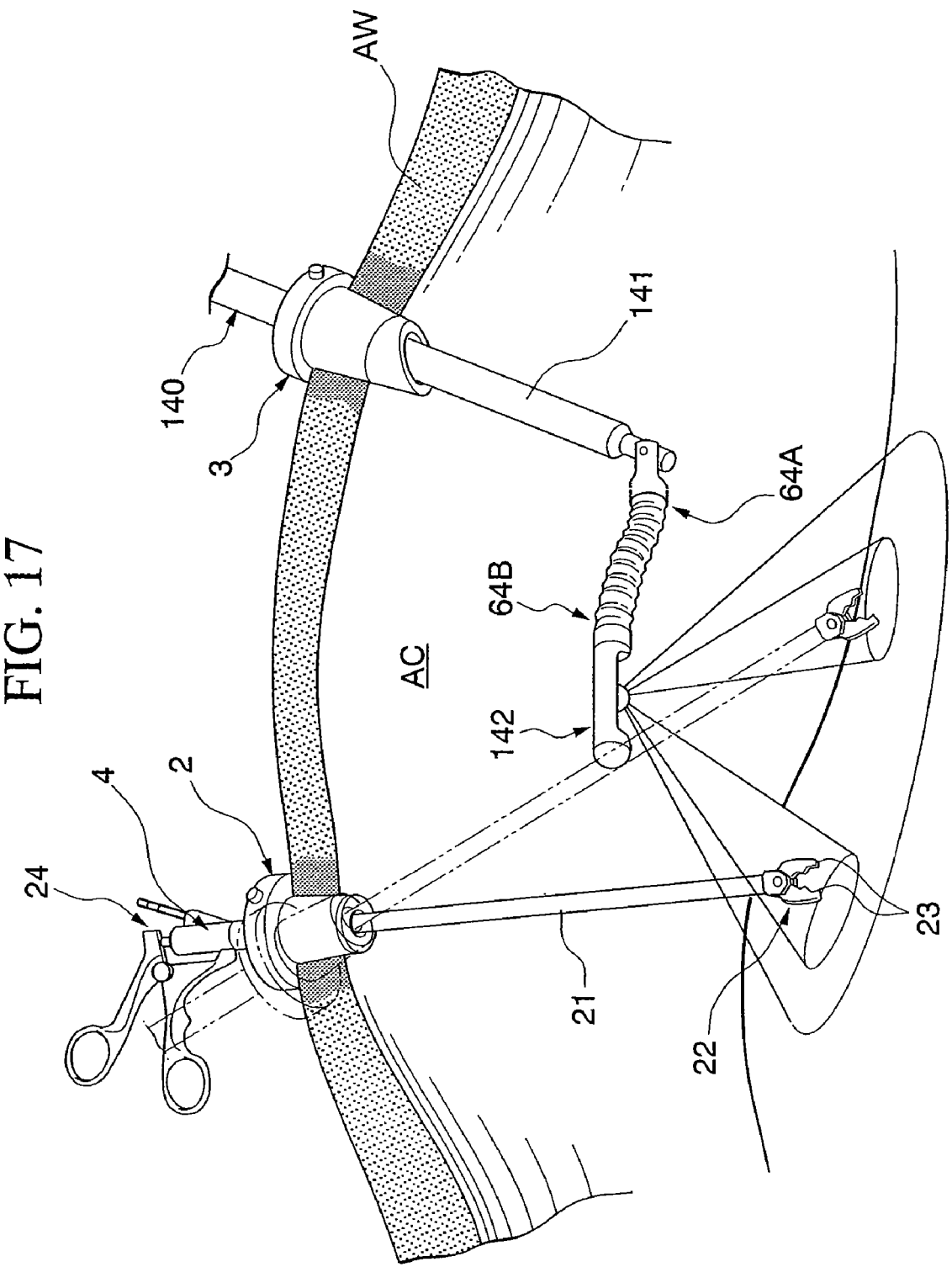
FIG. 17 is a view showing another embodiment of an endoscope.

Moreover, it is also possible for the insertion portion 141 to be a multi-stage bending type that has two bending portions 64A and 64B as in the case of the endoscope 140 shown in FIG. 17. The respective bending portions 64A and 64B have the same structure as that of the bending portion 64 described above, and the bending thereof is controlled either manually or by the endoscope drive section 108. Furthermore, a side view type of image pickup device 142 is provided at a distal end of this endoscope 140. The image pickup device 142 has a side view type of structure in which the direction of the field of view is substantially orthogonal to the axis of the insertion portion 141, while the component elements thereof other than the direction of the field of view are substantially the same as those in the above described image pickup device 65. In addition to this, it is also possible for the endoscope to have no bending portion, or for the endoscope to be a diagonal view type in which the direction of the field of view of the image pickup device intersects the axis of the insertion portion. In a multi-stage bending type of endoscope, if the bending is controlled such that the center of the field of view of the image pickup device 142 moves in parallel with the direction of movement of the treatment tool, then the same effects as those described above can be obtained. Moreover, because bending is possible in multiple stages, it is easy to preserve the angle α in the observation range solely by performing a bending operation.

Note that if treatment is to be performed using a plurality of treatment tools, the number of trocars may be three or more. In this case, it is preferable if a structure is employed in which the treatment tools observed by the endoscopes 5 and 140 can be set by the angle of observation conditions setting device 101. In this embodiment, because the position of the distal end of a treatment tool is specified using information from the trocars, by using a plurality of treatment tools, even if a particular treatment tool enters into a blind spot of the endoscopes 5 and 140, the treatment tools are not lost from view.

Second Embodiment

Figure 18:
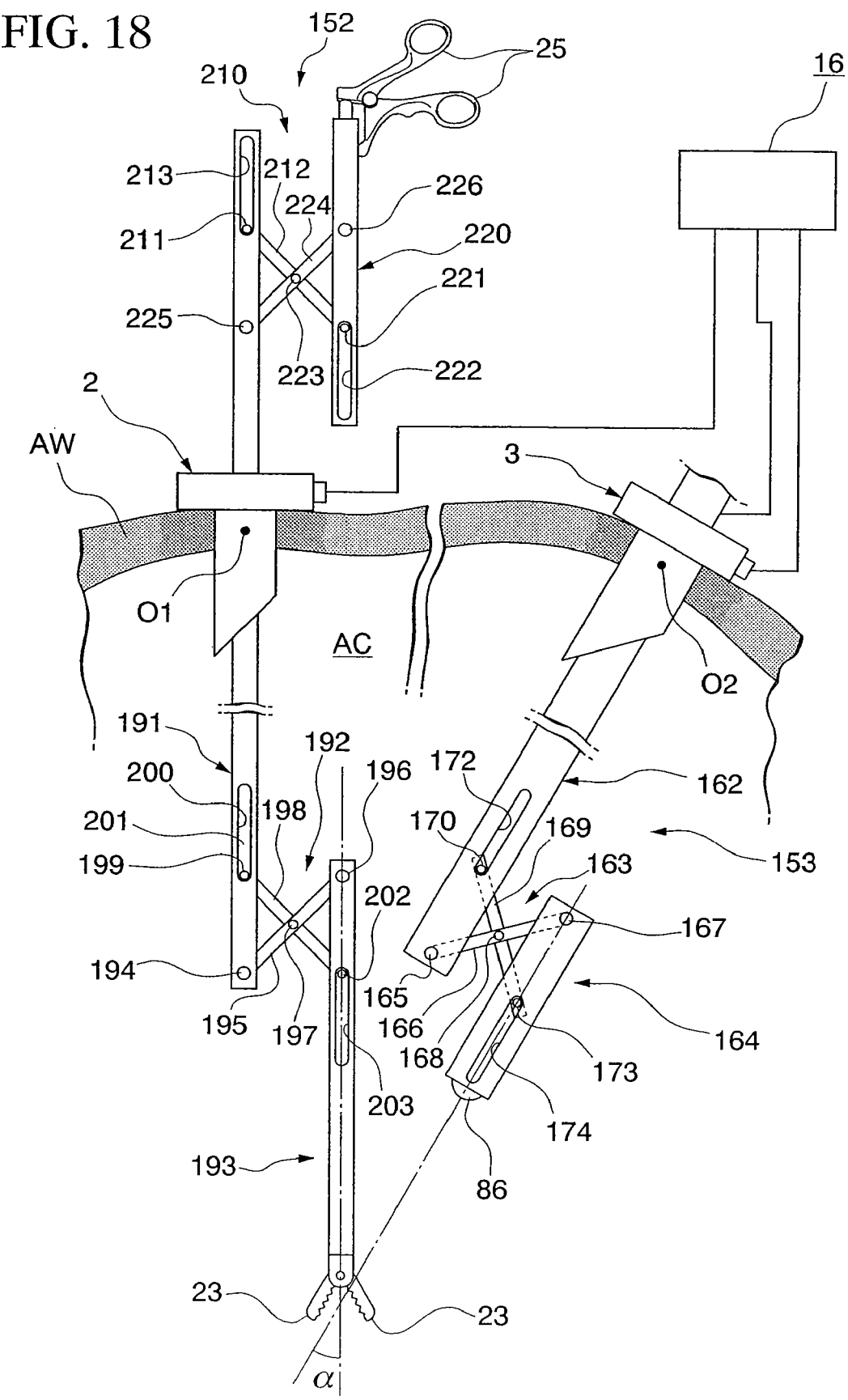
FIG. 18 is a view illustrating the placement during treatment in a structure in which both the treatment tool and the endoscope can be offset.

As is shown in FIG. 18, in this embodiment, a treatment system 151 has the system control unit 6, the first and second trocars 2 and 3, a treatment tool in the form of forceps 152, and an observation device in the form of an endoscope 153. In this structure, the forceps 152 and the endoscope 153 are both capable of being offset.

Figure 19:
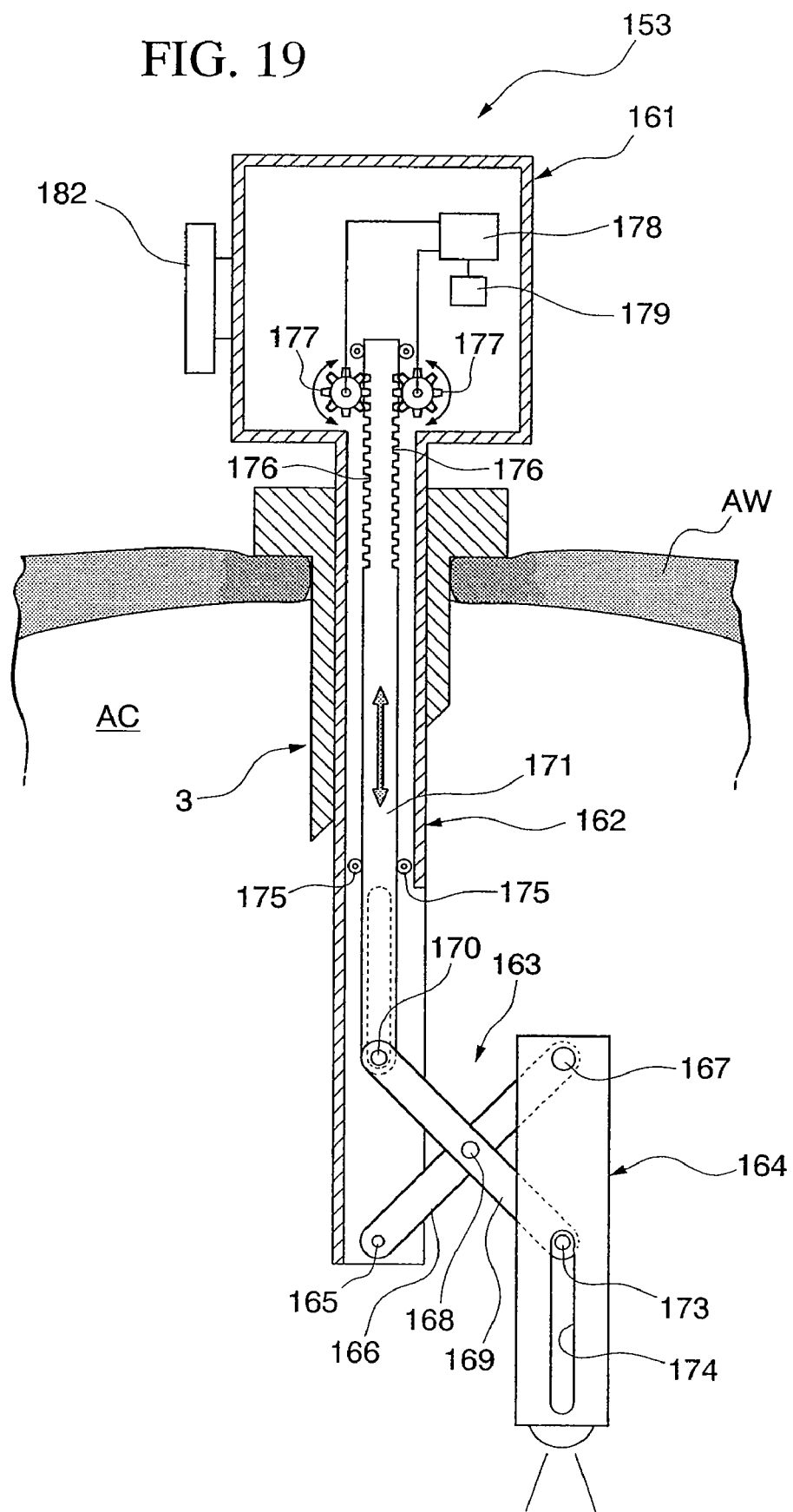
FIG. 19 is a cross-sectional view illustrating the structure of an endoscope that can be offset.

As is shown in FIGS. 18 and 19, the endoscope 153 has an insertion portion 162 that extends from an operating section 161 and is inserted into the abdominal cavity AC. An image pickup device 164 is mounted via a switching device in the form of an offset device 163 on a distal end of the insertion portion 162. The offset device 163 has a first lever 166 that is rotatably supported by a pin 165 at the distal end portion of the insertion portion 162. The first lever 166 extends from the end portion thereof that is axially supported by the pin 165 and the other end portion thereof is rotatably supported by a pin 167 on the image pickup device 164. A second lever 169 is rotatably mounted via a pin 168 substantially in the center between the one end portion and the other end portion of the first lever 166. One end portion of the second lever 169 is concealed inside the insertion portion 162 and is linked by a pin 170 to a pusher 171. The pin 170 is located further to the base end side than the pin 165, and is supported such that it can slide freely in an elongated hole 172 that is provided extending in the longitudinal direction of the insertion portion 162. The other end portion of the second lever 169 is supported on the image pickup device 164 via a pin 173. The pin 173 is located further to the distal end side than the pin 167, and is inserted such that it can slide freely in an elongated hole 174 that is provided extending in the longitudinal direction of the image pickup device 164. The image pickup device 164 is placed substantially in parallel with the insertion portion 162 and, in the same way as is shown in FIG. 6, a CCD 82, a magnifying optical system 83, a zoom apparatus 84, and an illumination apparatus 85 are provided at the distal end of the image pickup device 164. The optical axis of this image pickup device 164 is set so as to be parallel with the longitudinal direction of the insertion portion 162.

The pusher 171 is supported so as to be able to move freely forward or backward in the longitudinal direction of the insertion portion 164 using a roller 175, and approaches the operating section 161 through the interior of the operating section 162. A plurality of gear teeth 176 are formed in two rows extending in the longitudinal direction at the end portion of the pusher 176 that is located inside the operating section 161, and pinions 177 mesh respectively with each of the gear teeth rows. The pinions 177 are joined to a rotation shaft of a motor 178 and, by causing the motor 178 to revolve, the pusher 171 can be moved forward or backward in the longitudinal direction of the insertion portion 162. An offset sensor 179 that detects an amount of offset of the image pickup apparatus 164 from the amount of rotation and the direction thereof is provided in the motor 178. A rotary encoder, for example, may be used for the offset sensor 179. The pinions 177 are also connected to a knob 180 that is provided on a side portion of the operating section 161, so that the pusher 171 can also be moved forward or backward manually.

The forceps 152 shown in FIG. 18 have an insertion portion 191 that is inserted into the abdominal cavity AC through the first trocar 2. A treatment portion 193 is attached via a first link mechanism 192 to a distal end of the insertion portion 191. The first link mechanism 192 has a first lever 195 that is supported at the distal end portion of the insertion portion 191 such that it can rotate freely around a pin 194. The first lever 195 extends from the end portion thereof that is axially supported by the pin 194 and the other end portion thereof is rotatably supported by a pin 196 on the treatment portion 193. A second lever 198 is rotatably mounted via a pin 197 substantially in the center between the one end portion and the other end portion of the first lever 195. One end portion of the second lever 198 is concealed inside the insertion portion 191 and is linked by a pin 199 to a pusher 200. The pin 199 is supported such that it can slide freely in an elongated hole 201 that is provided extending in the longitudinal direction in the insertion portion 191. The other end portion of the second lever 198 is supported on the treatment portion 193 via a pin 202. The pin 202 is inserted such that it can slide freely in an elongated hole 204 that is provided extending in the longitudinal direction of the treatment portion 193.

The pusher 200 is supported so as to be able to move freely forward or backward inside the insertion portion 191, and the second lever 198 is connected to a distal end portion of the pusher 200. A second link mechanism 210 is connected to the base end portion of the pusher 200 at the base end side of the insertion portion 191. The second link mechanism 210 has a second lever 212 that is connected via a pin 211 to the pusher 200. The pin 211 is supported such that it can slide freely in an elongated hole 213 that is formed extending in the longitudinal direction in the base end portion of the insertion portion 191. The other end portion of the second lever 212 is concealed inside an operating section 220 and is connected to the operating section 220 via a pin 221. The pin 221 is supported such that it can slide freely in a hole 222 that is formed extending in the longitudinal direction of the operating section 220. A first lever 224 is also connected via a pin 223 to a substantially center portion between the one end portion and the other end portion of the second lever 212. One end portion of the first lever 224 is axially supported by a pin 225 at a base end portion of the insertion portion 191. The other end portion of the first lever 224 is axially supported by a pin 226 at the operating section 220.

The operating section 220 has a pair of freely opening and closing handles 25, and an operating component is connected to the handles 25. This operating component passes through the second link mechanism 210, the insertion portion 191, and the first link mechanism 192 in that order and enters the treatment portion 193. The treatment portion 193 is placed substantially in parallel with the longitudinal direction of the insertion portion 191, and a pair of forcep components 23 are mounted on the distal end of the treatment portion 193 such that they can open and close freely. The operating component is connected to the pair of forcep components 23 and opening and closing operations thereof are governed by the opening and closing of the handles 25.

When providing treatment, the first and second trocars 2 and 3 are inserted through the abdominal wall AW. The endoscope 153 is inserted into the second trocar 3 after the knob 180 has been rotated such that the image pickup device 164 is positioned on substantially the same straight line as the insertion portion 162. Once the image pickup device 164 has been inserted into the abdominal cavity AC through the second trocar 3, the knob 180 is rotated so that the image pickup device 164 is offset from the insertion portion 162. The pinions 177 are rotated so that the pusher 171 is moved forward and pushes the second lever 169. The offset device 163 then opens up and the image pickup device 164 is offset from the insertion portion 164. In this state, calibration is performed using the adjustment tool 110 in the same way as in the first embodiment. The position of the image pickup device 164 of the endoscope 153 is calculated from the angle of inclination of the second trocar 3, the insertion amount of the endoscope 153, and the amount of offset of the image pickup device 164 from the insertion portion 162. The amount of offset of the image pickup device 164 from the insertion portion 162 is detected using the amount of rotation of the pinions 177.

Once calibration is completed, the adjustment tool 110 is withdrawn and replaced by the forceps 152. The forceps 152 are inserted after the treatment portion 193 has been positioned so as to be on the substantially the same straight line as the insertion portion 191. Once the treatment portion 193 has been inserted inside the abdominal cavity AC, the operation section 220 is drawn away from the insertion portion 191 so that the second link mechanism 210 is opened. The pusher 200 then moves forward so that the first link mechanism 192 is opened and the treatment portion 193 is offset from the insertion portion 191. The amount by which the treatment portion 193 is offset can be ascertained by providing a sensor that measures the amount of movement of the second lever 212 and the amount of forward or backward movement of the pusher 200. Accordingly, the position of the distal end of the forceps 152 or, in this case, the position of the forcep components 23 can be calculated taking the base point O1 of the second trocar 2 as a reference from the insertion amount and angle of inclination of the forceps 152 that are detected by the first trocar 2 and from the offset amount of the treatment portion 193. Because the position of the base point O1 of the first trocar 2 as seen from the endoscope 153 is already known from the calibration, the system control unit 6 is able to ascertain both the observation position 164 of the endoscope 153 and the position of the distal end of the forceps 152.

Figure 10:
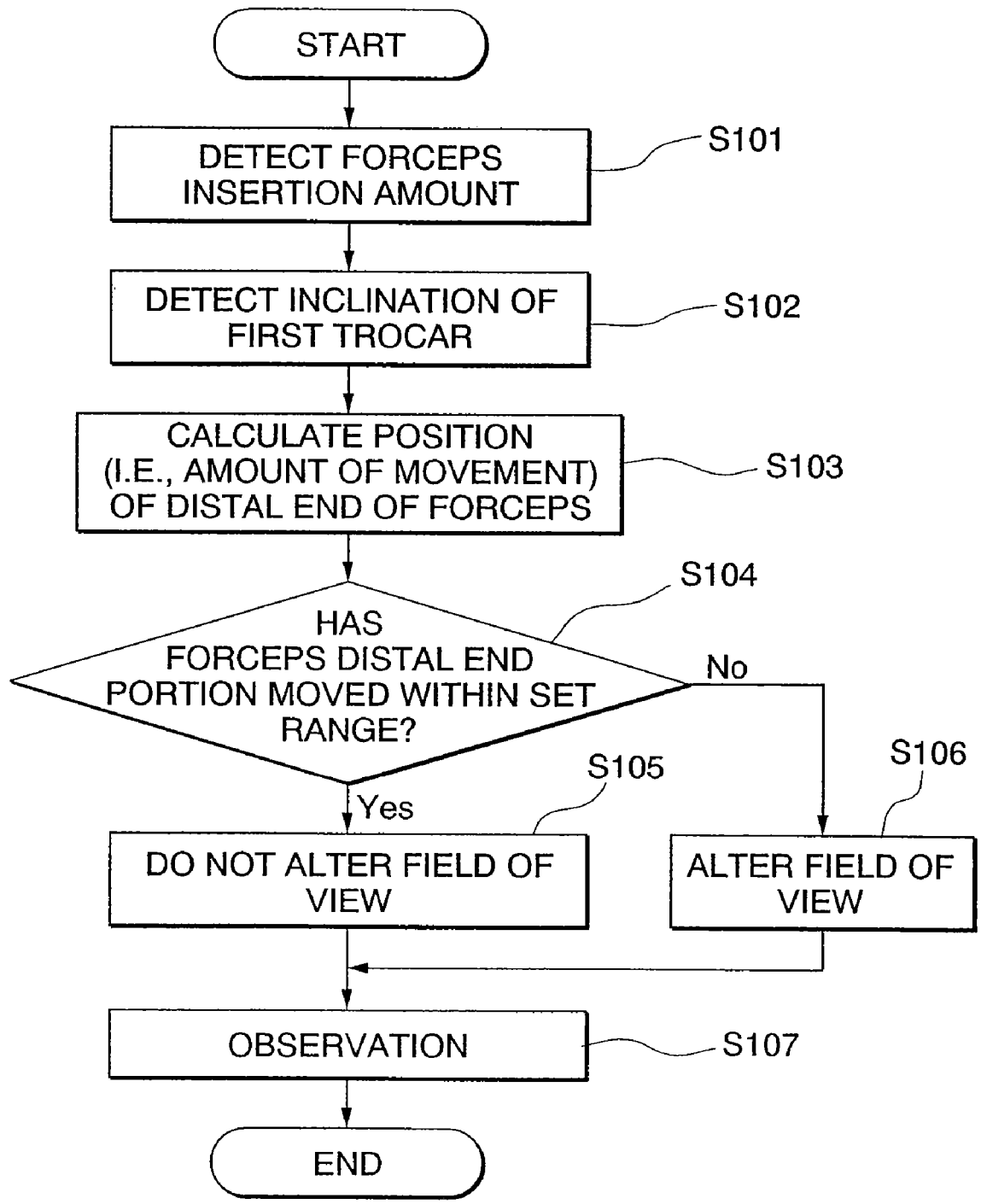
FIG. 10 is a flow chart illustrating processing during an observation.

The control to display observation images from the endoscope 153 either in synchronization with or not in synchronization with the position of the distal end of the forceps 4 is the same as in the first embodiment that was described using FIG. 10 and the like. The offset operation of the endoscope 153 can be made to track the movement of the forceps 4 by employing a suitable combination of cutting out an image using image processing and performing zoom adjustment in the same state as in the first embodiment when the bending portion is bent such that the direction of the field of vision moves in parallel (see FIG. 14).

In this embodiment, the same effects as those of the first embodiment can be obtained when the endoscope 153 and the forceps 152 have a structure that enables them both to be offset. It is also possible to employ a structure in which one of the endoscope 153 and the forceps 152 is capable of being offset and the other one has a fixed shape or is able to be bent.

Third Embodiment

This embodiment is characterized by the fact that the position of the distal end of a treatment tool in the form of the forceps 4 is displayed in an area stipulated on the monitor 115.

Figure 20:
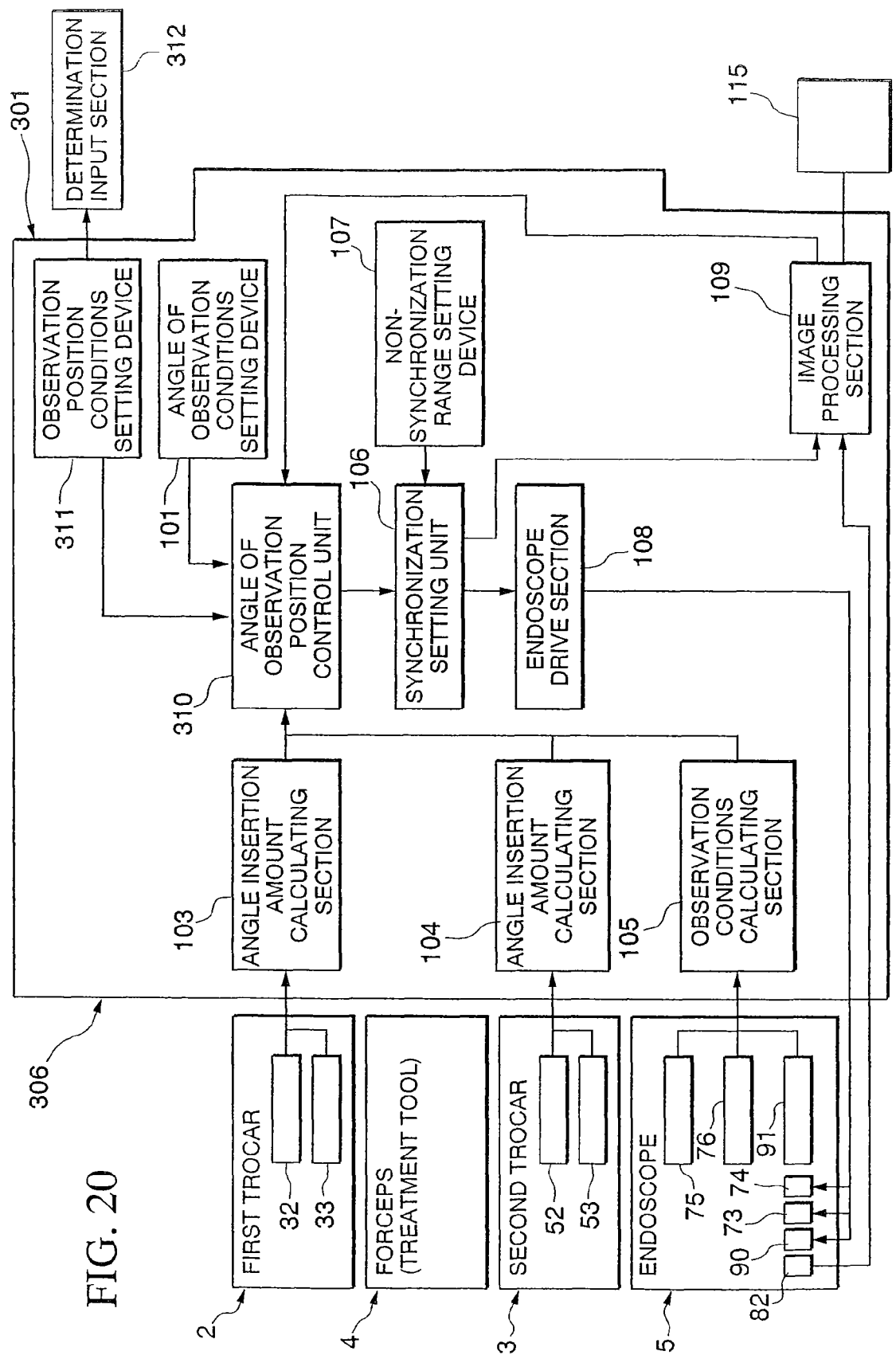
FIG. 20 is a block diagram showing a structure for displaying a treatment tool in a predetermined position.

As is shown in FIG. 20, a treatment system 301 has a system control unit 306 that is connected to each of the trocars 2 and 3 and to the endoscope 5. The system control unit 306 has an angle of observation position control unit 310 so that a position for displaying the distal end position of the forceps 4 within the observation range can be set. The angle of observation position control unit 310 receives information from the angle insertion amount calculating sections 103 and 104 and the observation conditions calculating section 105, and calculates the position of the forceps 4 and the position of the image pickup device 65 of the endoscope 5. The angle of observation position control unit 310 also calculates image pickup conditions such that a display screen can be obtained in which the distal end of the forceps 4 is located at a position set by an observation position conditions setting device 311.

The observation position conditions setting device 311 sets a position specified by an operator or the like using a determination input section 212 as an observation position, and delivers information about that position to the angle of observation position control unit 310. Examples of the determination input section 312 include a pointing device such as a mouse, a keyboard, or an input device such as a pointer.

Figure 21:
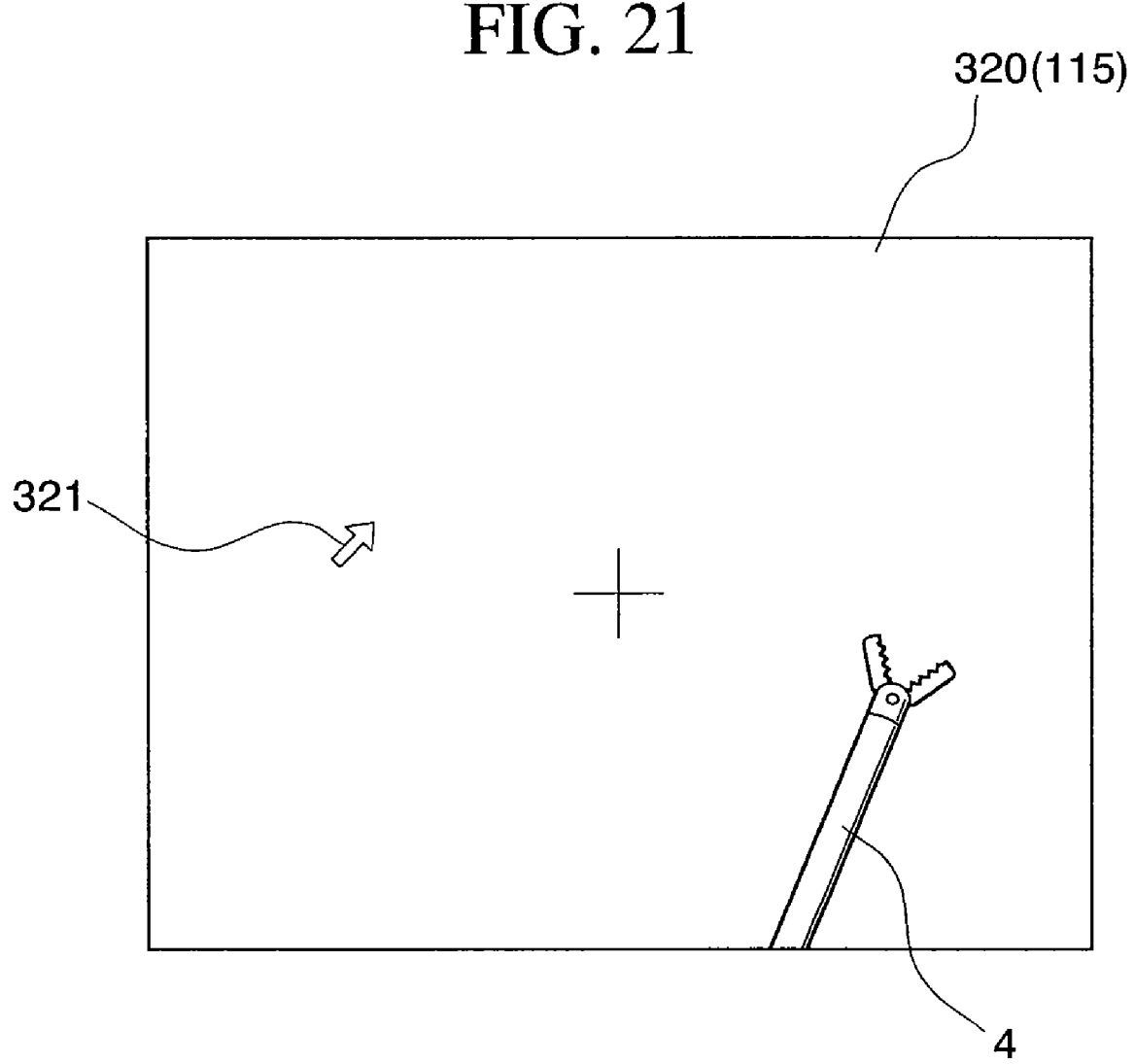
FIG. 21 is a view illustrating an example of an operation to set a position for displaying an endoscope.

When providing treatment using this treatment system 301, after calibration has been performed in the same way as is described above, a position for displaying the position of the distal end of the forceps 4 within the observation range (i.e., the observation range that is displayed on the monitor 115) is input using the determination input section 312. An example of an input when the determination input section 312 is a mouse is shown in FIG. 21. The pointer 321 of the mouse is moved over an observation range 320 that is displayed on the monitor 115 to a position above and to the right of the center of the observation range 320, and is then clicked. As a result, the coordinates for the position of the pointer 321 are registered as a set position in the observation position conditions setting device 311. The angle of observation position control unit 310 then calculates a position for the image pickup device 65 of the endoscope 5 such that the distal end of the forceps 4 that had been displayed on the left hand side in FIG. 21 move to the specified position. In addition, an optical zoom is set for the image pickup device 65 and processing conditions are set for the image processing section 109.

At this time, if the angle a was set in the angle of observation conditions setting device 101, then the position of the image pickup device 65, the magnification, and the image processing conditions are calculated so that the angle a is preserved. Moreover, if it is determined that synchronization needs to be performed by the synchronization setting device 106, the position of the distal end of the forceps 4 is displayed at the set position by the endoscope drive section 108 or the image processing section 109. If there is any subsequent movement in the position of the forceps 4, the amount of this movement is calculated and the forceps 4 are continuously displayed at the set position.

If an area is set for non-synchronization by the non-synchronization range setting device 107, then the range of the forceps is not altered to track the forceps 4 inside the area that was set as a non-synchronization area and is centered on the set position.

The registering of the set position may be performed prior to the insertion of the forceps 4 and it may also be altered partway through an operation. It is also possible to employ a structure in which, if a set position is not registered by the observation position conditions setting device 211 then it may still be displayed as an initial position in the center of the observation range.

According to this embodiment, it is possible to display the position of the distal end of a treatment tool in an area that is arbitrarily set on a screen, and it is possible to continuously secure a field of view that enables treatment to be performed more easily by an operator. The remaining effects are the same as those of the first embodiment.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

What is claimed is:

1. A treatment system comprising:
a first guide component that is used to insert a treatment tool into a body cavity;
a second guide component that is used to insert an observation device into the body cavity;
a tilt sensor that is provided in the first guide component and detects an angle of inclination of the treatment tool that has been inserted inside the first guide component;
an insertion amount sensor that is provided in the first guide component and detects an amount that the treatment tool has been inserted inside the first guide component;
a switching device that switches an observation range of the observation device such that the distal end of the treatment tool is displayed in an area that is set within an image of an interior of the body cavity being displayed on a display unit using the observation device that are acquired by the observation device that has been introduced into the body cavity; and
a system control unit that drives the switching device so that the observation device tracks a position of a distal end of the treatment tool by defining the position of the distal end of the treatment tool in a three-dimensional coordinate system whose point of origin is a base point provided in the second guide component by using parameters of another three-dimensional coordinate system whose point of origin is a base point provided in the first guide component based on information about the angle of inclination and insertion amount of the treatment tool.

2. The treatment system according to claim 1, wherein the switching device includes a bending portion of the observation device that is bent inside a body cavity.

3. The treatment system according to claim 1, wherein the switching device includes a zoom apparatus that changes an optical magnification of an image that is picked up.

4. The treatment system according to claim 1, wherein the switching device includes an offset apparatus that causes the image pickup device of the observation device to be offset from the insertion direction of the guide component.

5. The treatment system according to claim 1, wherein there is provided an input apparatus that sets an angle for the direction of the field of view in order to fix the direction of the field of view of an image that is displayed using the observation device relative to the position of the distal end of the treatment tool.

6. The treatment system according to claim 1, wherein the system control unit has a structure that prohibits switching of the observation range of the observation device if the amount of movement of the treatment tool is within a predetermined range.

7. The treatment system according to claim 6, wherein the switching device includes a bending portion of the observation device that is bent inside a body cavity.

8. The treatment system according to claim 6, wherein the switching device includes a zoom apparatus that changes an optical magnification of an image that is picked up.

9. The treatment system according to claim 6, wherein the switching device causes the image pickup device of the observation device to be offset from the insertion direction of the guide component.

10. The treatment system according to claim 6, wherein there is provided an input device that is used to set a range in which switching of the observation range of the observation device is prohibited.

11. A treatment method, comprising:
inserting a treatment tool into a body cavity through a first guide component that has been made to pierce an abdominal wall;
detecting an insertion amount when the treatment tool is inserted through the first guide component;
detecting an angle of inclination of the first guide component;
inserting an observation device into the body cavity through a second guide component that has been made to pierce the abdominal wall; and
switching an observation range of an image of the body cavity interior which is displayed on a display unit and which is acquired by the observation device that has been introduced into the body cavity based on an angle of inclination and an insertion amount of the treatment tool so that the image is displayed in an area that is set and so that the observation device tracks a position of a distal end of the treatment tool by defining the position of the distal end of the treatment tool in a three-dimensional coordinate system whose point of origin is a base point provided in the second guide component by using parameters of another three-dimensional coordinate system whose point of origin is a base point provided in the first guide component.

12. The treatment method according to claim 11, wherein the step of switching the field of view of the observation range of image includes a step of moving the observation device such that the direction of the field of view in the display image is the same both prior to and after a movement of the treatment tool.

13. The treatment method according to claim 11, wherein the step of switching the observation range of the image inside the body cavity includes a step of changing a magnification of the displayed image prior to and after a movement of the treatment tool.

14. The treatment method according to claim 11, wherein the step of switching the observation range of the image inside the body cavity includes a step of changing a range that is displayed in an acquired image prior to and after a movement of the treatment tool.

15. A calibration method that is used to correlate a position of a guide component that pierces an abdominal wall in order for a treatment tool to be introduced into a body cavity with a position of an observation device inserted into the body cavity, comprising the steps of:
acquiring an insertion amount and an angle of inclination of an adjustment tool inserted into a body cavity through the guide component;
acquiring an image of the distal end component of the adjustment tool using the observation device;
calculating a position and size of the distal end component using image processing; and
calculating a position of the guide component based on the position and size of the distal end component acquired at three or more different positions and from the insertion amount and angle of inclination of the adjustment tool at each position.

* * * * *